(12) United States Patent
Mani

(10) Patent No.: US 6,755,951 B1
(45) Date of Patent: Jun. 29, 2004

(54) ELECTRODIALYSIS OF SALTS FOR PRODUCING ACIDS AND BASES

(75) Inventor: K. N. Mani, Basking Ridge, NJ (US)

(73) Assignee: Archer-Daniels-Midland Company, Decatur, IL (US)

(*) Notice: Subject to any disclaimer, the term of this patent is extended or adjusted under 35 U.S.C. 154(b) by 164 days.

(21) Appl. No.: 09/837,498

(22) Filed: Apr. 18, 2001

Related U.S. Application Data

(62) Division of application No. 09/193,626, filed on Nov. 17, 1998, now Pat. No. 6,331,236.
(60) Provisional application No. 60/093,558, filed on Jul. 21, 1998.

(51) Int. Cl.[7] .............................................. B01D 61/44
(52) U.S. Cl. ...................... 204/523; 204/524; 204/529; 204/530; 204/531; 204/537; 204/538
(58) Field of Search ................................ 204/523, 524, 204/529, 530, 531, 537, 538

(56) References Cited

U.S. PATENT DOCUMENTS

| | | | |
|---|---|---|---|
| 3,475,122 A | 10/1969 | McRae et al. .................. 23/178 |
| 4,082,835 A | 4/1978 | Chlanda et al. .............. 423/242 |
| 4,107,015 A | 8/1978 | Chlanda et al. ........... 204/180 P |
| 4,390,402 A | 6/1983 | Mani et al. ............... 204/180 P |
| 4,536,269 A | 8/1985 | Chlanda et al. ........... 204/182.4 |
| 4,584,077 A | 4/1986 | Chlanda et al. ........... 204/182.4 |
| 4,592,817 A | 6/1986 | Chlanda et al. ........... 204/182.4 |
| 4,615,780 A | 10/1986 | Walker ....................... 204/538 |
| 4,636,289 A | 1/1987 | Mani et al. ............... 204/182.4 |
| 4,976,838 A | 12/1990 | Mani et al. .................. 210/651 |
| 5,049,250 A | 9/1991 | Chlanda .................... 204/182.4 |
| 5,135,626 A | 8/1992 | Mani et al. ................. 204/538 |
| 5,162,076 A | 11/1992 | Chiao et al. ................. 204/534 |
| 5,198,086 A | 3/1993 | Chlanda et al. ............. 204/534 |
| 5,200,046 A | 4/1993 | Chlanda et al. ............. 204/534 |
| 5,228,962 A | 7/1993 | Mani et al. .................. 204/534 |
| 5,281,317 A | 1/1994 | Mani et al. ................... 95/186 |
| 5,324,403 A | 6/1994 | Kennedy et al. ............ 204/525 |
| 5,814,498 A | 9/1998 | Mani et al. ................. 435/136 |
| 5,972,191 A | 10/1999 | Mani ........................... 204/631 |
| 6,110,342 A | 8/2000 | Mani ........................... 204/527 |
| 6,221,225 B1 | 4/2001 | Mani ........................... 204/523 |
| 6,294,066 B1 | 9/2001 | Mani ........................... 204/523 |
| 6,331,236 B1 | 12/2001 | Mani ........................... 204/525 |

OTHER PUBLICATIONS

Anonymous, "Sodium Sulfate Split to Caustic, Sulfuric," *Membrane & Separation Technology News* 15:2–4, BCC, Inc. (1996).

Mani, K.N., "Electrodialysis Water Splitting Technology," *J. Mem. Sci.* 58:117–138, Elsevier Science Publishers (1991).

Primary Examiner—Arun S. Phasge
(74) Attorney, Agent, or Firm—Sterne, Kessler, Goldstein & Fox P.L.L.C.

(57) ABSTRACT

An electrodialysis cell is operated in the presence of organic compounds that binds or chelates with the multivalent metals to form a metal chelating buffer. Among other things, this binding or chelating reduces power consumption, produces a stable cell operation, and avoids a fouling of the membranes while significantly improving membrane life, reliability, and operating costs. When a chelating agent is added to a salt solution containing multivalent cations, the chelating agent strongly binds with the cations, forming large size complexes. An ion exchange membrane retains these complexes within the compartment of the electrodialysis cell containing the feed solution. The multivalent cations is greatly inhibited from being transported across the cation exchange membrane, thus reducing the fouling of the cation membranes. Concurrently, the precipitation of the metals transported to the base loop is substantially abated.

13 Claims, 11 Drawing Sheets

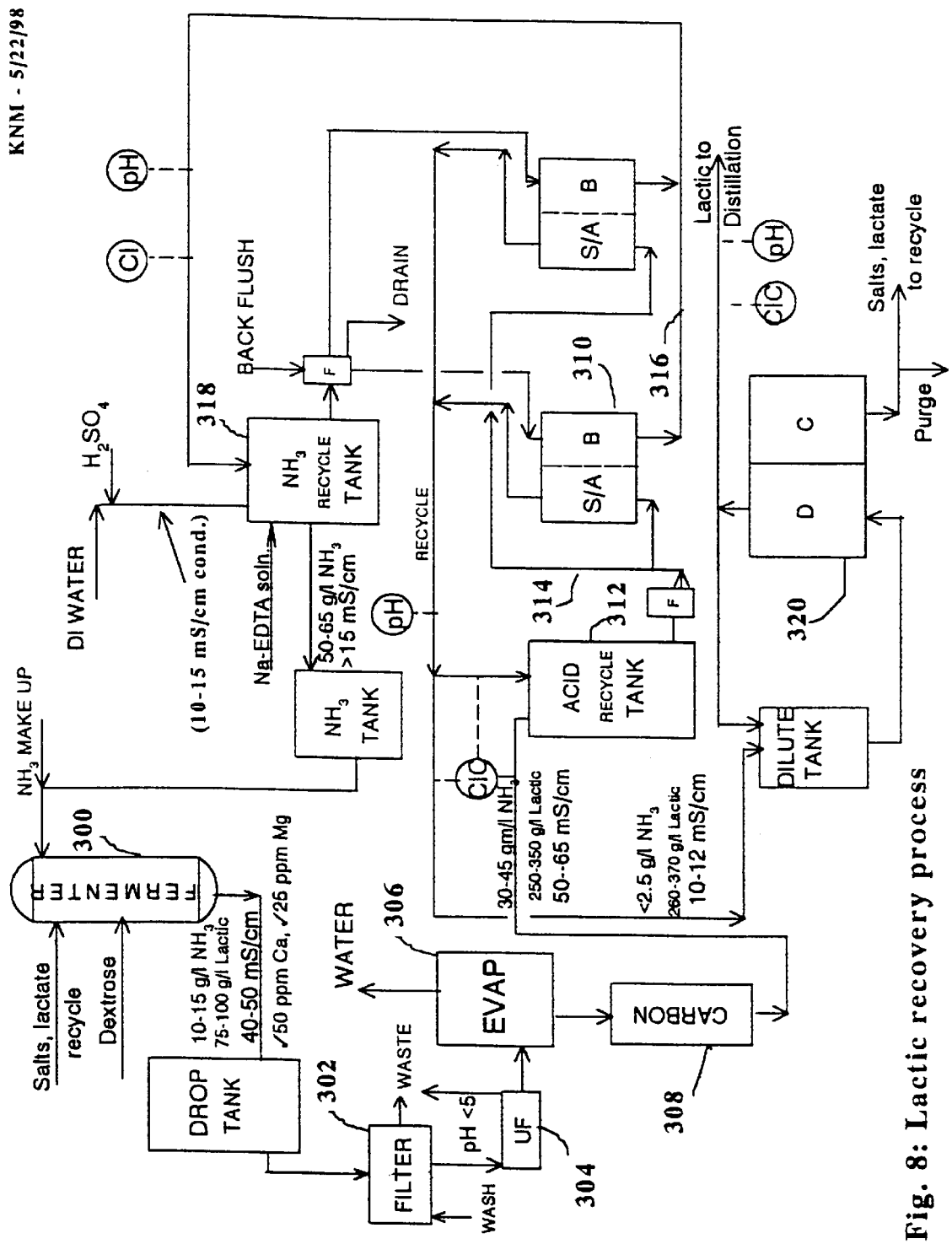
Fig. 8: Lactic recovery process

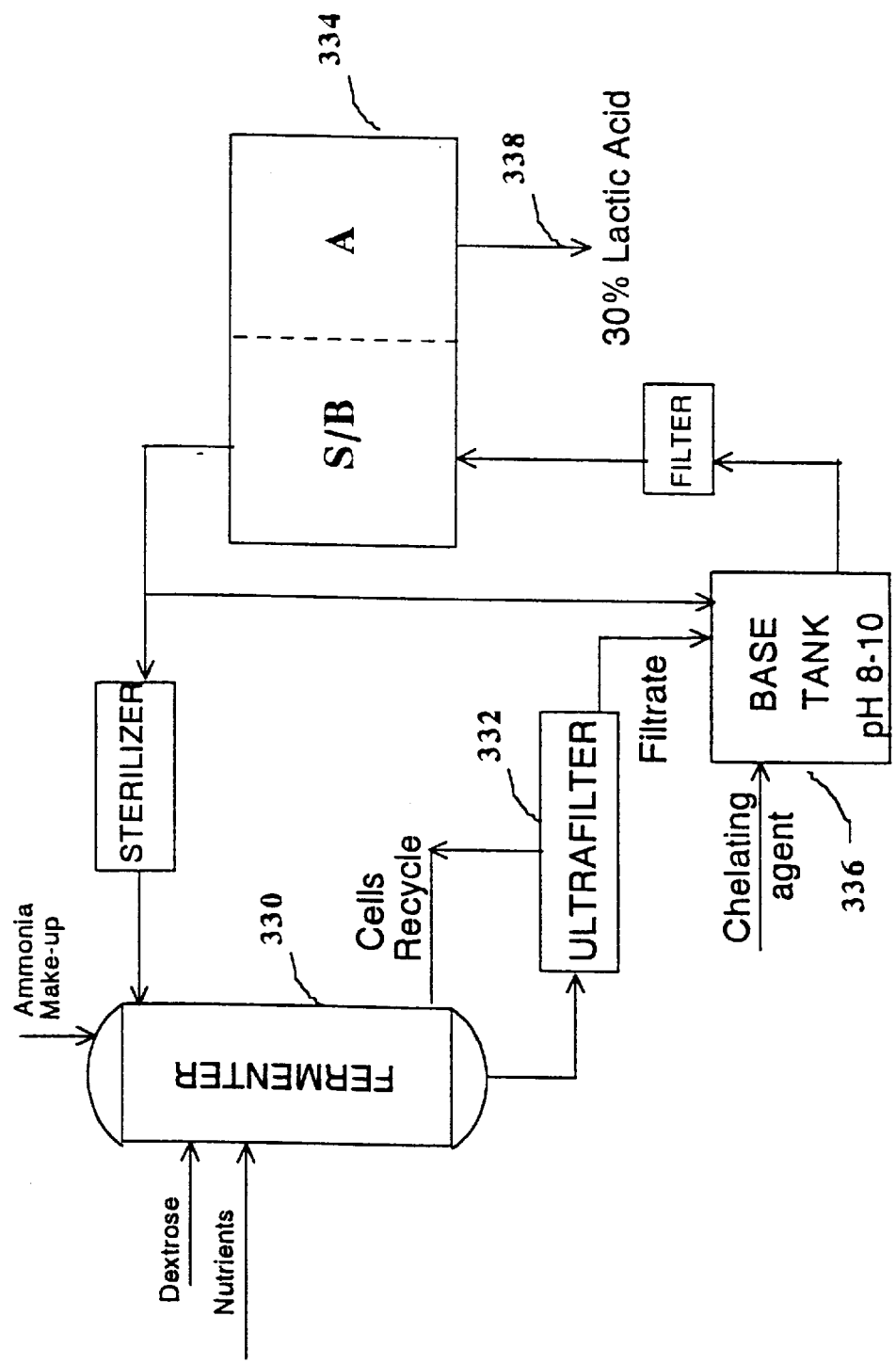
Fig. 8(a) Continuous fermentation with Lactic Acid recovery

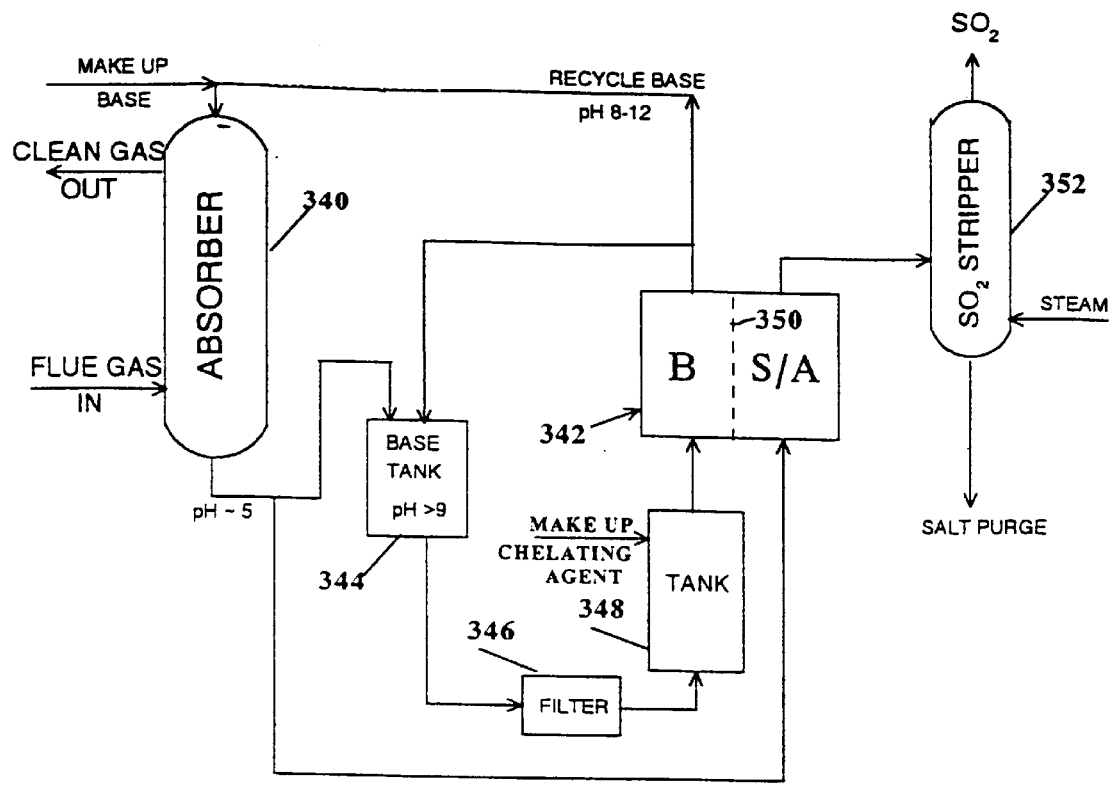
Fig. 9: SO₂ RECOVERY PROCESS
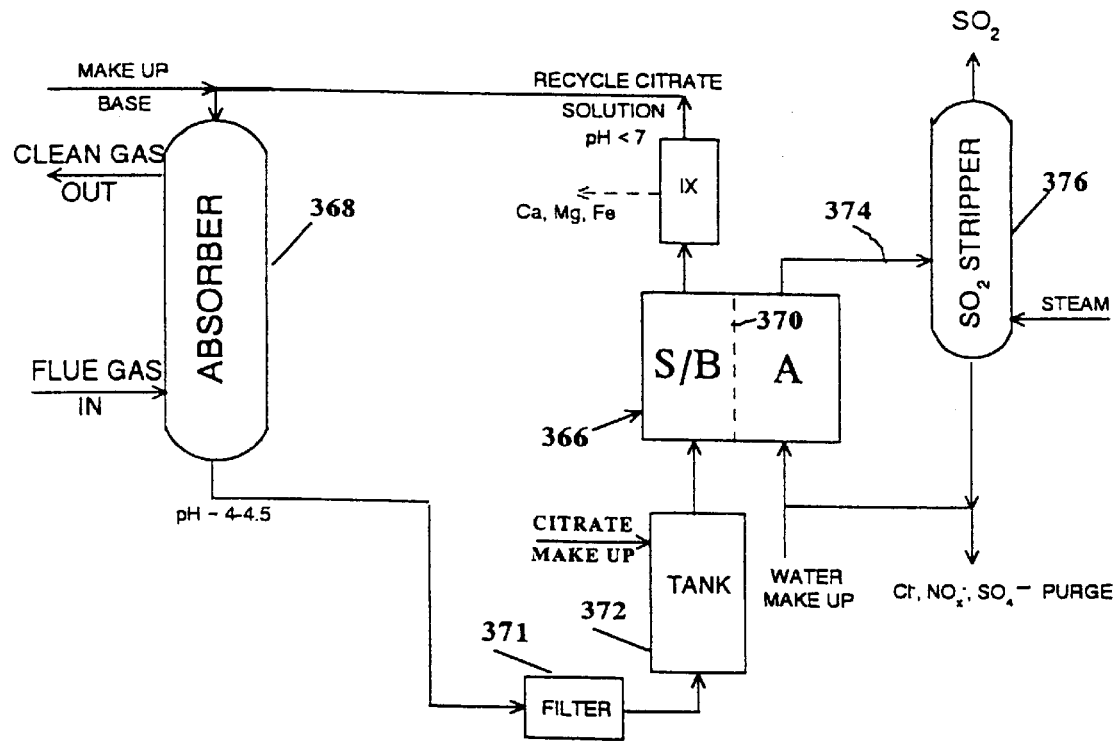
Fig. 10 CITRATE SCRUBBING WITH ED RECOVERY OF SO₂

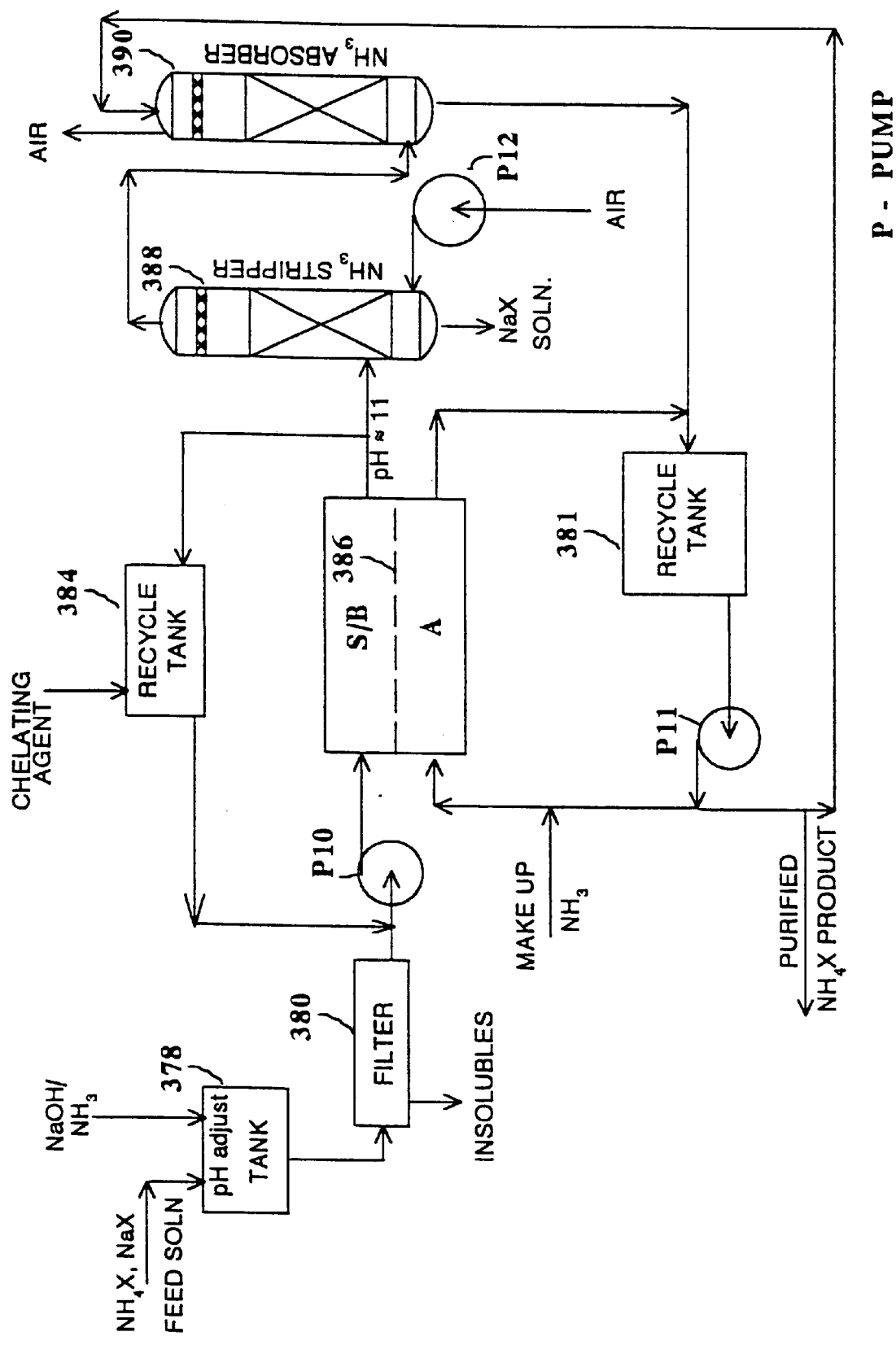
Fig. 11: AMMONIUM SALT PURIFICATION

ELECTRODIALYSIS OF SALTS FOR PRODUCING ACIDS AND BASES

This application is a division of U.S. application Ser. No. 09/193,626, filed Nov. 17, 1998, now U.S. Pat. No. 6,331, 236, which claims the benefit of U.S. Provisional Application No. 60/093,558, filed Jul. 21, 1998.

This invention relates to improved processes and methods for electrodialysis of salts to produce acids and bases.

BACKGROUND OF THE INVENTION

For general information, reference is made to my earlier U.S. Applications "ELECTRODIALYSIS APPARATUS," Ser. No. 08/784,050, filed Jan. 17, 1997 and "APPARATUS AND PROCESS FOR ELECTRODIALYSIS OF SALTS," Ser. No. 08/787,899 filed Jan. 23, 1997.

The invention relates to a use or addition of certain organic acids, particularly polyaminoacetic acids, in order to enhance the retention in a solution of divalent cations in the pH range of 2 or higher. The stoichiometric complexes, called "chelates," formed with the multivalent cations, are effectively retained in a solution by an ion exchange membrane so that they are not transported out of a given process loop. The primary benefit of this procedure is that the divalent metals are kept in the solution within a given loop of the electrodialysis cell and, more particularly, in the vicinity of bipolar membranes used in cells, as described in my earlier applications. This retention, in turn, has a remarkably beneficial effect on the cell's operation in terms of improving the process' reliability, reducing power consumption and avoiding heating/melting problems.

Nanofiltration, chelating resin ion exchange, or other pre-treatments may be used in conjunction with the electrodialysis step to reduce the divalent and multivalent metals content in a salt feed stream or a base product stream. Within the electrodialysis cell itself, monovalent selective cation membranes may be used to further reduce the amount of divalent metals transported out of the feed loop and thereby reduce the amount of a chelating agent needed to retain the divalent metals in the transported product (usually higher pH) solution.

The invention enables essentially the same process to be used in many different systems, without requiring an extensive modification thereof. More particularly, the inventive process may be used in these and a number of other applications such as (a) the production of acids, organic or inorganic, in conjunction with a weak base such as ammonia. In this context, the invention is particularly well suited to a recovery of lactic acid from a fermentation derived ammonium lactate, especially a recovery in a two compartment cell, (b) recovery of sulfur dioxide from waste gases using a two compartment cation or anion cell, and (c) purification of ammonium salts for use in a fluid catalytic cracking ("FCC") catalyst production using a two compartment anion cell, and (d) production of acids and bases in a three compartment cell.

Salts are byproducts or intermediate products of a number of chemical processes. Regenerable flue gas desulfurization processes use a sodium alkali to absorb the $SO_2$, thus resulting in a soluble bisulfite salt, $NaHSO_3$. Fermentation processes for organic acids (such as acetic and lactic acids) go through the intermediate production of salts, such as ammonium acetate or lactate. For example, the manufacturing of rayon/regenerated cellulose results in a generation of significant quantities of byproduct sodium sulfate.

Electrodialysis ("ED") may be used to convert these and other soluble salts directly into their acid and base components. For example, in the case of organic salts, such a procedure will enable a direct recovery of the organic acid in a relatively pure form, while the co-product base (ammonia for example) may be recovered for reuse in the fermentation process in order to make pH adjustment. Thus, there is an economical and environmentally superior option for producing organic acids. In other instances, such as with sodium bisulfite or sodium sulfate, electrodialysis offers an environmentally superior route for recovering and/or recycling the acid, base components Electrodialysis uses direct current as a means for causing a movement of ions in a solution. Electrodialysis processes are carried out in a stack arrangement comprising a plurality of flat sheet ion exchange membranes. To produce acids and bases from their salts, the process unit requires a means for splitting water. Two useful means for splitting water into hydrogen ($H^+$) and hydroxyl($OH^-$) ions are:

(i) A bipolar membrane or a bipolar module including a combination of cation and anion membranes functioning as a bipolar membrane. Suitable bipolar membranes are available from Aqualytics, a division of Graver Water and Tokuyama Corporation.

(ii) An electrode set comprising an anode and a cathode. The electrodes, (particularly the anodes), are suitably coated for chemical stability, for minimizing power consumption, and for the formation of byproducts other than hydrogen (at cathode) and oxygen( at the anode). Suitable electrodes are available from Eltech Corporation, Electrode Products Inc., and others. One can also use a hydrogen depolarized anode to generate the H+ions in the aqueous solution and next to the anode.

When using a stack of bipolar membranes, the stack contains electrodes (anode and cathode) at either end of a series of membranes and gaskets which are open in their central area in order to form a multiplicity of compartments separated by the membranes. Usually, a separate cleaning solution is supplied to end compartments which contain the electrodes with special membranes placed next to the electrodes to prevent a mixing of the process streams with the electrode cleaning streams.

The majority of the stack between the electrode compartments comprises a repeating series of units of different membranes with solution compartments between adjacent membranes. The repeating unit is called a "unit cell" or simply a "cell". A solution is usually supplied to the compartments either by internal manifolds formed as part of the gaskets and membranes or by a combination of internal and external manifolds. The stacks can include more than one type of unit cell. Streams may be fed from one stack to another stack in order to optimize process efficiency. The change in the composition of a stream after one pass through the stack may be relatively small.

The solutions can be recycled by being pumped to and from recycle tanks. An addition of fresh solution to and withdrawal of product from the recycle loop can be made either continuously or periodically in order to control the concentration of products in a desired range.

A known treatment of aqueous salt streams by electrodialysis (or electrolysis) forms an acid or a base from the salt. In order for a bipolar membrane, to function as a water splitter, the component ion exchange layers must be arranged so that the anion selective layer of each membrane is closer than the cation selective layer to the anode. A direct current is passed through the membranes in this configuration to cause water splitting with $OH^-$ ions being produced on the anode side and a corresponding number of $H^+$ ions being produced on the cathode side of the membranes. The dissociated salt anions move toward the anode and the dissociated salt cations move toward the cathode.

The electrolysis process works in a similar manner, with the water splitting occurring at the two electrodes. When a direct current is passed, water molecules are converted to oxygen gas at the anode along with an introduction of H$^-$ ions into the aqueous solution. At the cathode, the water molecules are converted to hydrogen gas along with the introduction of OH ions into the aqueous solution. In the hydrogen depolarized anode based electrolysis unit, OH$^-$ ions are released into the aqueous solution next to the cathode, while the released hydrogen gas is forwarded to the catalytic hydrogen depolarized anode for H$^+$ ion generation.

Electrodialysis equipment for acid and base production has three compartment cells comprising bipolar, cation and anion membranes, two compartment cells containing bipolar and cation membranes, a multichamber two compartment electrodialysis cells comprising bipolar and two or more cation membranes (or two or more anion membranes). A number of processes uses such equipment.

SUMMARY OF THE INVENTION

In keeping with an aspect of the invention, I have found that operating an electrodialysis cell in the presence of organic compounds binds or chelates with the multivalent metals to form a metal chelate buffer that dramatically enhances the performance of electrodialysis cells. Among other things, this binding or chelating reduces power consumption, produces a stable cell operation, and avoids a fouling of the membranes. These benefits translate into a significantly improved membrane life, improved process reliability, and reduced operating costs for the processes.

The chelating agent binds with the multivalent metal ions (calcium, magnesium, iron, etc.). When a chelating agent is added to feed solutions containing multivalent cations, the chelating agent strongly binds with the cations, forming larger size complexes. The ion exchange membranes retain these complexes within the compartment containing the feed solution. The multivalent cation transport across the cation exchange membranes is substantially inhibited. As a result, the fouling of the cation membranes is reduced or eliminated. Concurrently, the precipitation of the metals transported to the base loop is substantially abated.

When added to the base product solution, the chelating agent binds with the multivalent cations that may be present in the feed stream or transported from an adjoining loop, and mitigates the precipitation of the multivalent cations either on the bipolar membranes or within the base compartment, thus allowing the water splitting process to occur in a trouble-free manner over extended operating periods.

BRIEF DESCRIPTION OF THE DRAWINGS

Preferred embodiments of the invention are shown in the attached drawings, in which:

FIGS. 1(a)–1(c) schematically show the construction of unit cells for two and three compartment electrodialysis cells using bipolar membranes;

FIG. 8 is a schematic which shows the use of this invention in the production of organic acid via a fermentation process;

FIG. 8(a) is a schematic which shows a process for a continuous production/recovery of organic acid;

FIG. 9 is a schematic which shows an improved process for sulfur dioxide recovery;

FIG. 10 is a schematic which shows a novel ED process for sulfur dioxide recovery; and FIG. 11 is a schematic which shows an improved process for ammonium salt purification.

Figure 1:
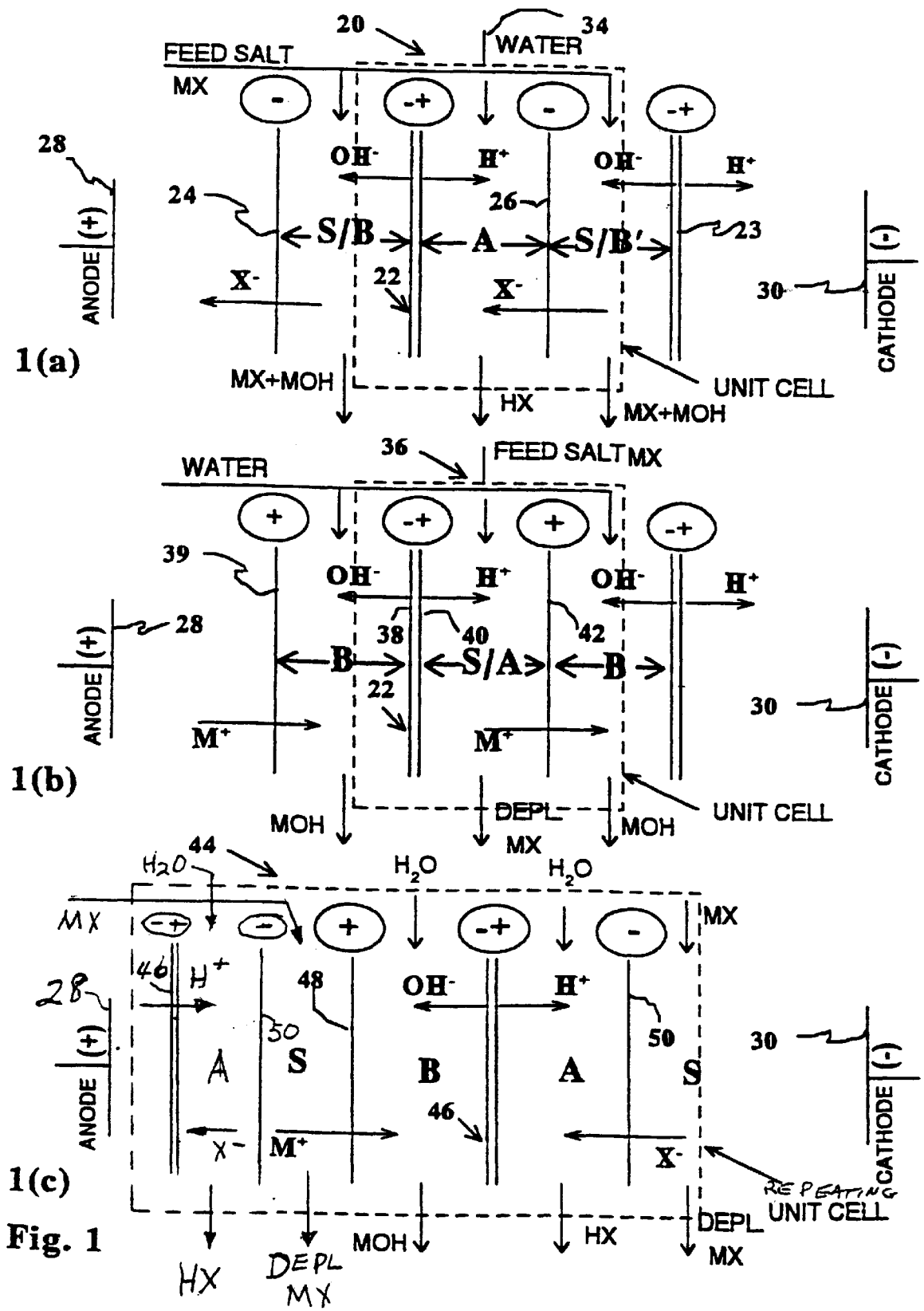
FIG. 1 shows the unit cell for the three most useful configurations. Specific references that may be read for more information are.

"*Electrodialysis Water Splitting Technology*" by K. N. Mani; J. Membrane Sci.,(1991), 58, 117–138

U.S. Pat. Nos. 4,082,835; 4,107,015; 4,390,402; 4,536, 269; 4,584,077; 4,592,817; and 4,636,289.

FIG. 1(a) shows a two compartment cell 20 comprising bipolar (designated as –+) membranes and anion membranes (designated as –). A salt/base compartment (S/B) is located between the anion surface of the bipolar membrane 22 and the anion membrane 24. An acid compartment (A) is located between the cation surface of the bipolar membrane 24 and another anion membrane 26. The combination of the two compartments S/B, A and these three membranes 24—24 is termed a "unit cell" or, simply, a "cell." As many as 200 or more cells may be assembled in series between an anode (+) 28 and a cathode(–) 30, in which case, the membranes outline in dashed lines in FIG. 1(c) would be repeated 200 times in order to make a complete drawing.

The salt solution is to be acidified. For example, a lactate solution MX is fed to the salt/base compartment (S/B), while a liquid comprising water may be supplied to the acid compartment (A). Under a direct current driving force from anode 28 to cathode 30, the bipolar membrane 22 splits the water, and in the process generates H$^+$ and OH$^-$ ions, as shown. Simultaneously, the X$^-$ anions from the dissociation of the salt MX are transported across the anion membrane to the acid compartment, where they combine with the H$^+$ ions to form the acid HX. The process may be represented schematically as follows:

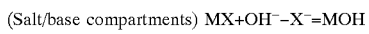
(Salt/base compartments) MX+OH$^-$–X$^-$=MOH

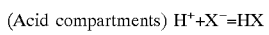
(Acid compartments) H$^+$+X$^-$=HX

The process has been detailed fully in my above-identified earlier patent applications. This process is best suited for processing salts of weak bases; particularly ammonium salts. The concentration of the acid product that can be made is typically 1–6 N; with the higher concentrations being feasible for weak organic acids (pK$_a$ of ~2.5 or greater). The feed salt concurrently becomes alkaline, with the pH being ~10–11 for ammonia production.

FIG. 1(b) shows a two compartment cell 36 comprising bipolar 22 and cation membranes 39, 42 (designated as +). A base compartment (B) is located between the anion surface 38 of the bipolar membrane 22 and the cation membrane 39. A salt/acid compartment (S/A) is located between the cation surface 40 of the bipolar membrane and another cation membrane 42. The combination of these membranes and the two compartments is termed a "cell." A stack of 200 or more such cells may be assembled between an anode 28 and a cathode 30, meaning that the structure in the dashed line box is repeated 200 times in series.

The salt solution to be acidified, an organic salt solution MX for example, is fed to the salt/acid compartment (S/A), while a liquid comprising water may be supplied to the base compartment (B). Under a direct current driving force from anode 28 to cathode 30, the bipolar membrane 22 generates $H^+$ and $OH^-$ ions, as shown. Simultaneously, the $M^+$ cations resulting from the dissociation of the salt MX are transported across the cation membrane 42 to the base compartment (B), where they combine with the $OH^-$ ions to form the base MOH. The process may be represented as:

(Acid compartments) $MX + H^+ - M^+ = HX$ (Base compartments) $M^+ + OH^- = MOH$ The extent of the conversion of salt that can be carried out efficiently by this arrangement is determined by the amount of current used (coulombs), the concentration of the salt solution, and importantly, by the $pK_a$ of the acid involved. For weakly dissociated acids with a $pK_a$ greater than about 2.5, the conversion can be 80 to ~97%. Most organic acids such as lactic, acetic, citric, formic and others fit into this category. The residual cation content in the acid product can then be removed, if necessary, via a conventional cation exchange resin.

FIG. 1(c) shows a three compartment cell 44 using bipolar 46, cation 48, and anion 50 membranes. Three compartments, acid (A), salt (S) and base (B) are located between the three membranes 46–50, as shown. The entire combination of membranes and compartments are termed a "cell." FIG. 1(c) has been drawn to show that the combination of compartments A, S, B, A, S . . . may be repeated any number of times. Hence, as with the two compartment cells outlined earlier, any suitable number of cells may be placed between a single set of electrodes.

This cell arrangement is the most generic for the production of acids and bases, particularly strong acids, such as hydrochloric and nitric and strong bases such as sodium hydroxide and potassium hydroxide. The salt solution is fed to the (S) compartment located between the cation and anion membranes, while a liquid comprising water is fed to the acid (A) and base (B) compartments located on either side of the bipolar membrane, as shown. Under a direct current driving force, the $H^+$ and $OH^-$ ions generated at the bipolar membrane are transported to the acid (A) and base (B) compartments, respectively. Concurrently, the $M^+$ ions are transported across the cation membrane to the base compartment, while the $X^-$ ions are transported across the anion membrane to the acid compartment. The net effect is the production of relatively pure acid (HX) and base (MOH) products from the salt MX.

$MX + H_2O = MOH + HX$

Other cell arrangements involving bipolar membranes in conjunction with two or more cation membranes or two or more anion membranes may also be used in processing salts where the pK of the product acid or base is in the intermediate range. Such cell arrangements convert the salt to acid and base at a higher current efficiency when compared with the two-compartment cells shown in FIGS. 1(a) and 1(b), but at higher capital and operating costs.

The operation of the process using electrodes as the source of $H^+$ and $OH^-$ ions is, often termed electrolysis and involves the co-production of $O_2$ and $H_2$ at the anode and cathode respectively. In operation, electrolysis is similar to the bipolar membrane electrodialysis described above. The main difference is that a unit cell includes the requisite cation and/or anion exchange membranes between an anode and a cathode. A number of cells, with each cell containing a set of electrodes may be assembled into a single process unit. The electrical and hydraulic connections between them may be made either in series or in parallel, so as to form a compact commercial process unit. Example references are:

Meliere, K. A., et. al., "Description and Operation of Stone & Webster/Ionics $SO_2$ removal and recovery" US NTIS Report, PB-242 573, (1974), 1109–26, and U.S. Pat. No. 3,475,122.

Figure 2:
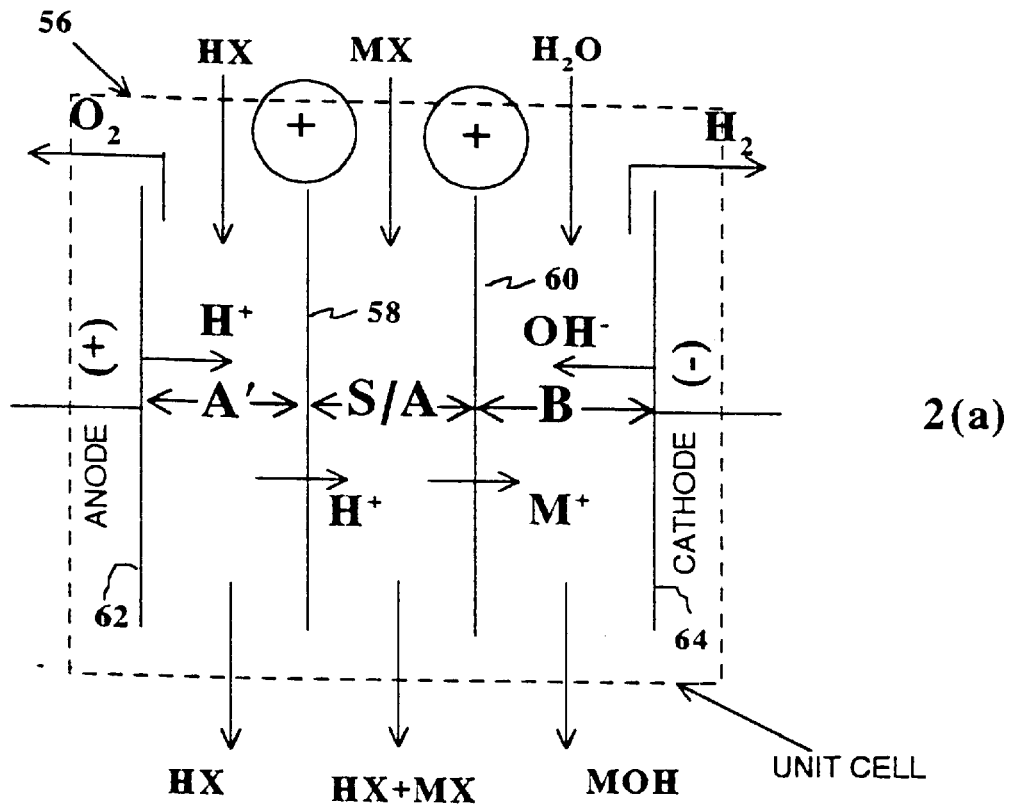
FIGS. 2(a), 2(b) show the construction of unit cells for two and three compartment cells using a set of electrodes.
Figure 2:
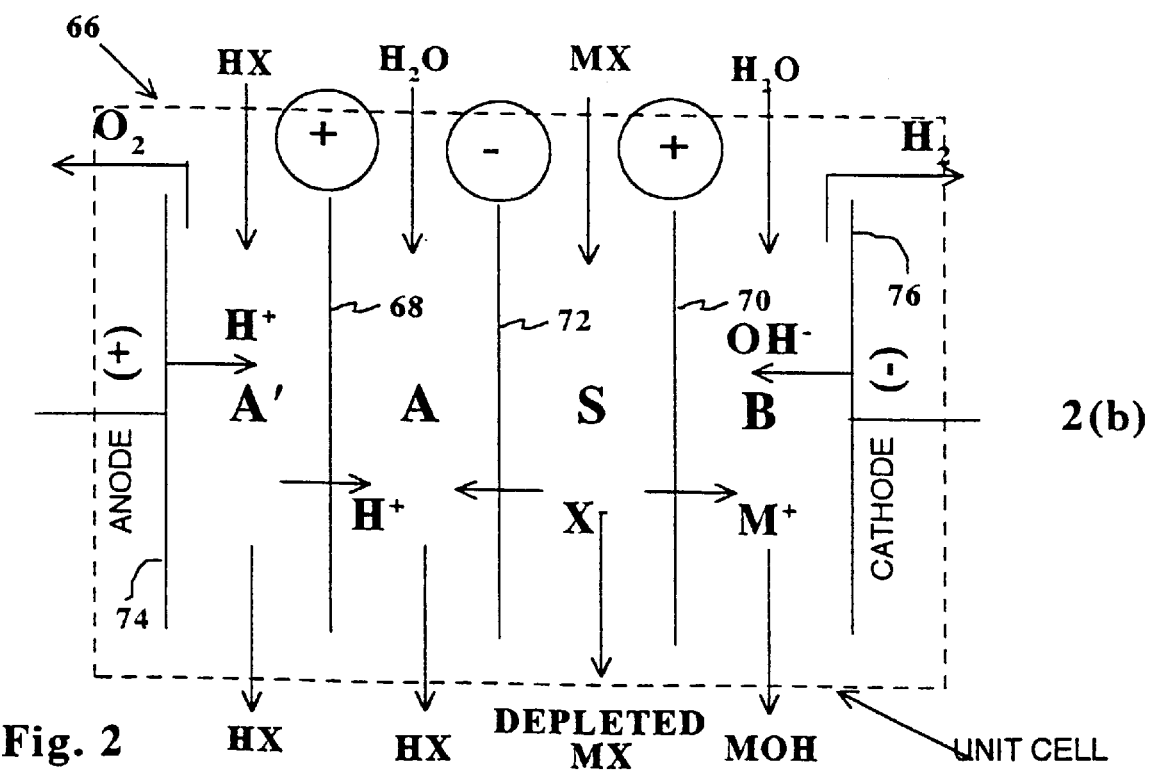

FIG. 2 shows two of the possible cell arrangements. FIG. 2(a) shows a cell 56 using two cation membranes 58, 60 and three compartments located between an anode (+) 62 and a cathode (−) 64. The operation of the process is similar to the operation of the two-compartment cation cell shown in FIG. 1(b) and is particularly applicable to the production of weak acids from their salts. A separate acidic stream may be circulated in the compartment (A'), which is a buffer compartment next to the anode. The salt stream which is to be processed is circulated in the compartment (S/A) between the two cation membranes 58, 60, as shown. This use of the buffer compartment (S/A) and the cation membranes used to contain it, is preferred particularly when an oxidation of the stream components is a problem. However, the buffer compartment is not essential to the operation of the two compartment cell.

A stream comprising water is circulated in the base compartment (B) next to the cathode. Under a direct current driving force, $H^+$ and $OH^-$ ions are generated at the anode (+) and cathode (−), respectively, along with oxygen and hydrogen co-products from the dissociation of water. Simultaneously, the $H^+$ ions are transported from compartment (A') across the first cation membrane to the intermediate salt/acid compartment (S/A) where it combines with the anion $X^-$ ions to form the acid HX. The $M^+$ cation is transported from compartment (S/A) across the second cation membrane ions 60 to the base compartment (B) to form the base MOH. The reactions may be summarized as follows:

(Buffer A' compartment) $H_2O = \frac{1}{2}O_2\uparrow + 2H^+ + 2e^-$
($H^+$ transported out across the first cation membrane)
(Salt/acid compartment) $2MX + 2H^+ - 2M^+ = 2HX$
(Base compartment) $2H_2O + 2e^- = 2OH^- + H_2\uparrow$
$2M^+ + 2OH^- = 2MOH$
(Overall) $2MX + 3H_2O = 2HX + 2MOH + H_2\uparrow + \frac{1}{2}O_2\uparrow$ FIG. 2(b) shows another version of the process using two cation membranes 68, 70 and one anion membrane 72 between an anode (+) and a cathode (−). The operation of this cell is similar to the operation of the three compartment cell shown in FIG. 1(c). The cell is capable of generating relatively pure acid and base. The salt MX is fed to the compartment (S) between the anion membrane 72 and the second cation membrane 70 as shown. The anion membrane separates the acid product from the feed stream salt. The operation of the cell is otherwise similar to the operation of the two-compartment cell shown in FIG. 2(a).

When the cells of FIG. 2 are compared with the bipolar membrane based cells shown in FIG. 1, the co-production of hydrogen and oxygen at the electrodes along with the acid and base products requires an additional energy input to the process of ~1.2 V/cell. An option that can reduce this power load is the use of a hydrogen depolarized anode in place of the conventional anode.

Figure 3:
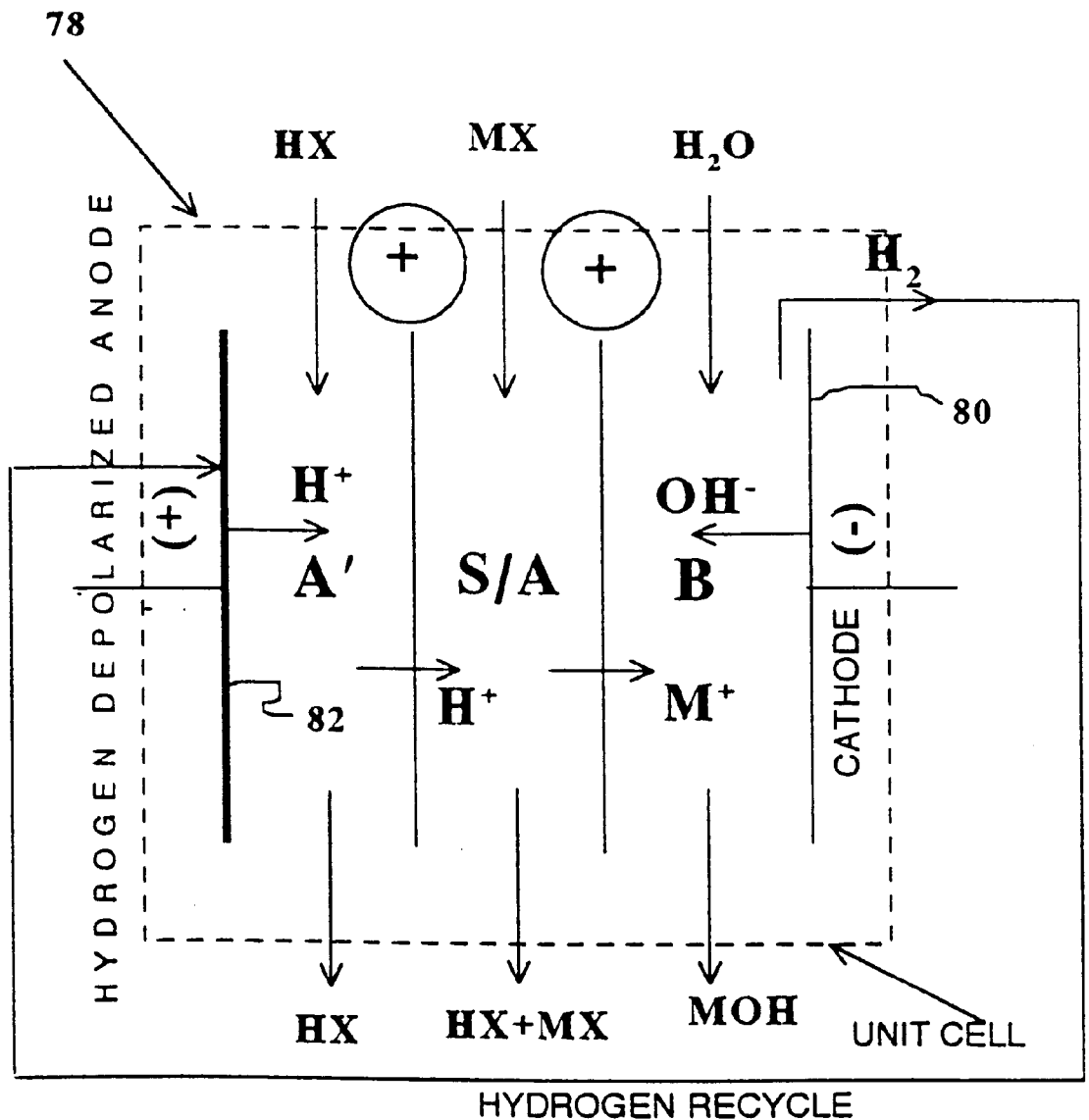
FIG. 3 schematically shows a two compartment cell using a hydrogen depolarized electrode.

FIG. 3 shows the construction of such a cell, which is conceptually identical to the cell of FIG. 2(a). In such a cell, the hydrogen gas produced at the cathode (−) 80 is returned to the anode (+) 82 and oxidized to protons at a gas diffusion electrode. The $H^+$ ions is released into the aqueous solution next to the gas diffusion electrode. This technique can lower the cell voltage by ~1 volt/cell; thus reducing the power consumption level to nearly the consumption level that is obtained with a cell using a bipolar membrane. (*Membrane & Separation Technology News,* (1996), 15(2), 2–4). Other cell configurations employing the gas diffusion anodes can be visualized by those skilled in the art.

For purposes of this patent disclosure, a number of structures will be considered equivalents. One such structure involves the operation of cells employing bipolar membranes which are a combination of cation and anion membranes that behave together as a bipolar membrane. Another structure has a set of electrodes generating $H^+$ and $OH^-$ ions. Still another is a hydrogen depolarized anode based cell that collects hydrogen gas at the cathode and injects it into a companion porous catalytic electrode to generate $H^+$. The term bipolar membrane, or its equivalent, will be used to denote any one of these options.

Despite the usual filtration/ultrafiltration and carbon treatment steps, a major problem in using the electrodialysis cells in the water splitting applications is that the feed salt contains a significant amount of di- and multivalent metal ions, particularly calcium and magnesium. When the feed stream is processed, as is, the metal ions are transported to the base loop of the electrodialysis unit and are precipitated there. The precipitation of these ions inside the base loop causes a plugging of the cells, a decreasing current throughput, and, in the extreme, a mechanical failure resulting from overheating and meltdown problems. In certain situations the divalent cations also precipitate within the cation membranes or bipolar membranes, this causing damage or irreversible fouling of the membranes.

The most commonly used method to ensure satisfactory cell operation is to treat the salt feed stream with a chelating cation exchange resin packed into a column (or several columns in series). The spent resin is then regenerated by using dilute acid and base. While quite effective, this method is an additional step that further increases the complexity and cost of the overall process. The cost of the chemicals and the disposal of the waste streams are also important issues.

Two earlier patent applications, Ser. No: 08/787,899 and Ser. No: 08/922,587, provide other options for solving the problems associated with the presence of multivalent metals in the feed solutions. The improvements disclosed therein are:

The use of nanofiltration prior to feeding the ED cell in order to reduce the total divalent metals content in the salt solution feed stream to become less than about 25 parts per million. This level was found to be low enough to avoid precipitation problems within the salt/base loop itself over extended periods of operation. The preferred operating pH range in the base loop is 7–13.5 and more preferably 7–11.

The use of an ion exchange column which is packed with a cation exchange resin in communication with the base loop of the electrodialysis cell. The column is capable of reducing the divalent metals concentration in the base loop to a low level so as to avoid their precipitation. If the ED cell were to use cation membranes, the multivalent metals level in the feed itself has to be at a suitably low level to prevent a fouling of the membranes. Since the cation exchange resin is capable of reducing the di- and multivalent metals level in the base loop to very low levels, the pH in the loop can cover a wider range, namely 7–14.

The use of a monovalent selective cation membrane that reduces the amount of divalent metal ions transported to the base loop. This, in turn, further reduces the multivalent metals load in the base loop. Combining this selective cation membrane step with either or both of the above steps (nanofiltration and ion/exchange column) substantially reduces or minimizes the precipitation of the multivalent metals inside the electrodialysis cell.

While satisfactory, the equipment and processes using the above features still have some drawbacks. The use of a nanofiltered feed stream by itself or in combination with only the monovalent selective cation membranes has limitations when the pH in the base loop is greater than about 10–11. This is because the surface of the bipolar membrane, wherein the OH- ions are generated, is at a pH of ~14. Consequently, unless there are very short path lengths and/or high flow rates and/or product dilution are used, there is an ever present tendency for a precipitation of multivalent metals and the problems associated therewith. The process is also restricted to salts of monovalent anions. The use of ion exchange column to treat the feed does eliminate these problems, but at a higher cost in terms of process complexity, maintenance requirements, and pumping power (i.e. higher pressure drop).

Therefore, there is a need for a simpler method for preventing the precipitation of the multivalent metals in the base loop and a fouling of the cation membrane when used.

A need also exists for an improved method which enables the base loop in the ED cell to operate over the entire pH range of 5–14 without precipitation problems within the base loop or on the surfaces of the bipolar membranes.

A number of processes disclosed in the prior art U.S. patent literature are difficult to operate because of the problems associated with the precipitation of multivalent ions in the base loop. A first example of these problems is the recovery of purified salt from a mixture containing a common anion, for example, ammonium sulfate from a mixture of ammonium sulfate and sodium sulfate. (See U.S. Pat. No. 5,228,962). Such streams exist as byproducts in the production of FCC catalysts. A second problem requires a process for flue gas desulfurization using a two compartment cation cell, wherein the sodium bisulfite is converted to sodium sulfite and sulfur dioxide. (See U.S. Pat. Nos. 4,082,835; 5,281,317). Any bisulfite that gets oxidized to sulfate when contacting the flue gas in an $SO_2$ absorber needs to be purged (causing a loss of reagent) or recovered in secondary three compartment cell. A third problem relates to a recovery of organic acids, particularly lactic acid from ammonium lactate via fermentation. This is disclosed in my above-identified pending applications. All of these processes would benefit from an improvement that obviates the multivalent metals precipitation problem.

A need exists for an improved regenerative flue gas desulfurization process that recovers the $SO_2$ as well as the alkaline reagent via a one step electrodialysis process. This would simplify the process and improve the economics of $SO_2$ recovery.

A need also exists for processes that do not require the use of an ion exchange column in communication with the base loop. The use of an ion exchange column, while effective, makes the process more complex and requires periodic shut downs for resin regeneration, as well as larger capacity pumps which accommodate the higher pressure drops in such a combined loop.

When dealing with the processing of salts of multivalent anions (e.g. sodium or ammonium sulfate), nanofiltration is not effective in reducing the multivalent metals in the solution. Hence, a need exists for a method of processing salt solutions without the use of nanofiltration, while minimizing or avoiding the problems associated with the fouling of the cation membranes (if used) and/or the precipitation of the multivalent metals in the high pH environment on the base side of the bipolar membrane.

In the production of caustic soda from sodium chloride or sodium sulfate using a three compartment cell, an improved process that obviates the need for the ion exchange step would simplify the process and therefore is highly sought after.

When processing organic compounds that bind or chelate with the multivalent metals, there is a dramatic enhancement of the performance of electrodialysis cells reflected in reduced power consumption, stable cell operation and a greatly reduced fouling of the membranes. As a result, there is a significantly improved membrane life, improved process reliability, and reduced operating costs for the processes. The chelating agent that binds with the multivalent metal ions (calcium, magnesium, iron, etc.) accomplishes one or more of the following:

When added to feed solutions containing the multivalent cations, the chelating agent strongly binds with the cations, forming larger size complexes. The ion exchange membranes substantially retain these complexes within the compartment containing the feed solution. Also, the multivalent cation transport across the cation exchange membranes is substantially inhibited. As a result, the fouling of cation membranes is reduced or eliminated. Concurrently, the precipitation of the metals upon transport to the base loop is also substantially abated.

When added to the base product solution, the chelating agent binds with the multivalent cations that may be present in the feed or transported from an adjoining loop, which mitigates the precipitation of the multivalent cations either on the bipolar membranes or within the base compartment. Thus, the water splitting process occurs in a trouble-free manner and over extended operating periods.

The complex formed by the chelating (sometimes termed "sequestering") agent as well as the chelating agent itself must be soluble and stable in the process solution. This is particularly important in the higher pH ranges where the multivalent metals would otherwise precipitate out. (S. Chaberek and A. E. Martell, *Organic Sequestering Agents*, John Wiley and Sons, Inc., New York, 1959). Some chelating agents have a low solubility at low pH values that could limit their use in the feed stream solution that would become acidic, particularly at the cation selective surface of the bipolar membrane.

Many organic compounds (such as lactic and citric acid) are soluble in water at low pH values, form complexes with metals, (particularly magnesium and iron), and have been found to be suitable for use in the pH range of 2–6. An organic acid, such as lactic, forms strong complexes with magnesium and calcium, thus substantially preventing their transport across the cation membrane. Polyaminoacetic acids and their salts are also effective in forming complexes or chelates with the multivalent cations, such complexes being stable at high pH values.

A chelating agent or compound (such as ethylenediamine tetraacetic acid (EDTA), for example) forms a strong complex with calcium (and other multivalent metals) that results in free calcium concentrations of less than 1 part per million in a solution in the pH range of 9–14 (Kirk Othmer Encyclopedia of Chemical Technology, $3^{rd}$ Edition Volume 6; pages 1–24). When an adequate amount of such an agent is added to the salt feed stream, the metal-chelate complex was found to be substantially retained by the bounding ion exchange membranes, thus ensuring that only extremely low concentrations of free calcium are available for transport and/or foul the cation membranes in the ED cell.

In a similar vein, the addition of an adequate amount of chelating agent to the base loop was found to enhance the retention of calcium and other multivalent metals in solution, thereby preventing or mitigating their precipitation within the loop or on the surfaces of the bipolar membranes, and enabling a long term trouble-free operation of the ED cell.

The improved cell operation resulting from the use or addition of the chelating agents has an applicability to a wide range of processes. Examples of these processes are:

(a) An improved Process for Recovering Lactic Acid from Ammonium Lactate Produced via Fermentation.

The salt is processed in a two compartment cation cell to convert 80–95+% of the salt to ammonia and lactic acid. The addition of the chelating agent to the ammonia (base) loop keeps the transported calcium, and magnesium in solution, thereby obviating the need for an ion exchange column in the base loop. Product ammonia, containing small amounts of the chelating agent (e.g., 200–500 ppm EDTA), can be recycled to the fermenter. Interestingly, the lactic acid itself is a chelating agent that substantially reduces the transport of the multivalent metals to the base loop. A monovalent selective cation membrane may optionally be used in the ED cell to further reduce the amount of multivalent metals transported to the base loop. The inventive process is an improvement over the process disclosed in my above-identified patent applications, Ser. No. 08/787,899 and Ser. No. 08/922,587, because neither nanofiltration to filter the feed stream nor an ion exchange column in the ammonia loop is required.

Product lactic acid from the two compartment cation cell contains small amounts of ammonium and other cations (sodium, potassium, calcium, magnesium) as well as anions such as chloride and sulfate (derived from the added water or nutrients). Substantially, all of these materials may have cations and anions removed (so as to obtain purified acid) via a desalting electrodialysis step, and optionally recycled back to either the fermenter or to the upstream two compartment cation cell. In this manner, essentially a 100% recovery of lactic and ammonia is achieved by the integrated process.

(b) A Process for Continuous Fermentation and Recovery of Lactic Acid Using a Two Compartment Anion Cell.

This is an improvement over the process as disclosed in my application, Ser. No: 08/639,831. The ammonium lactate from the fermenter is processed in a two compartment anion cell to recover the lactic acid as a concentrated solution. The basified lactate at a pH of 6–11 is returned to the fermenter. A suitable chelating agent such as EDTA (which has a higher chelating capacity than lactic itself, particularly at the higher pH levels) is added to the salt/base loop of the ED cell. As with the process (a) above, the added chelating agent is consumed by the microbes/fungi in the fermenter. The improved process obviates the need for nanofiltration of the feed stream and will be applicable to mono- as well as multivalent organic acids.

(c) An Improved Process for Purifying Ammonium Salts.

Salt mixtures (ammonium nitrate/sodium nitrate and ammonium sulfate/sodium sulfate) are generated as byproducts in the production of FCC catalysts. The presence of multivalent metal impurities interferes with the proper operation of the two compartment anion cell as disclosed in the U.S. Pat. No. 5,228,962. In the inventive process, a chelating agent is added to the salt feed stream in quantities sufficient to complex with the multivalent cations present therein. Through this manner of operation, the cell performance is dramatically improved.

(d) An Improved Process for Flue Gas Desulfurization.

The sulfur dioxide in a flue gas stream is absorbed in a sodium sulfite rich solution containing an added chelating agent (such as citric acid, EDTA), or a mixture of two or more chelating agents. A sodium bisulfite rich stream is produced and processed in a two compartment cation cell to obtain a sulfite rich stream that is recycled to the $SO_2$ absorber, while the $SO_2$-rich stream from the acid compartment of the cell is stripped to recover the $SO_2$ in a concentrated form. The chelating agent(s) prevent the precipitation of the multivalent metals within the base loop of the cell, and possibly reduce the amount of byproduct sulfate in the absorber. A portion of the solution after the $SO_2$ recovery, which is primarily sodium sulfate, is purged from the process in order to maintain the sulfur balance and prevent an accumulation of the multivalent cations. Optionally, this stream may be suitably purified and processed in a three compartment cell to obtain caustic soda and sulfuric acid.

(e) A Novel Flue Gas Desulfurization Process Using a Two Compartment Anion Cell.

The flue gas containing sulfur dioxide is scrubbed with a solution containing a chelating agent and an active alkali (e.g. sodium citrate or a sodium sulfite rich solution containing a suitable chelating agent). The absorption of $SO_2$ results in the formation of bisulfite. The use of a citrate scrubbing solution is favored because of its ability to buffer the scrubber pH in the range of 4–6, thereby substantially eliminating scale formation in the $SO_2$ scrubber/absorber. Additionally, the citrate scrubber system is known to generate very low levels of byproduct sulfate (*SRI Process Economics Program,* Report No: 63B, Chapter 6, March 1980), which in turn improves the $SO_2$ recovery.

The bisulfite rich solution from the scrubber is processed in a two compartment anion cell, with a portion of the bisulfite being transported to the acid loop in order to form sulfurous acid (from which $SO_2$ is recovered by a stripping operation) while the remainder is basified in the salt/base loop and returned to the absorber.

One advantage of this process is that the low pH (i.e. 4–6) of the regenerated liquor ensures an availability of adequate amounts of bisulfite ions that are preferably transported to the acid loop, thereby enabling good process efficiency. Another key advantage of this process is that the sulfate byproduct as well any chlorides and nitrates/nitrites (from $No_x$ scrubbing ) are also removed with the sulfurous acid in the acid loop, thus enabling essentially 100% recovery of the active alkali and the chelating agent in a single step. An accumulation of multivalent metals is avoided by taking a small purge stream or by the use of an ion exchange or precipitation step.

(f) An Improved Process for Producing Sodium Hydroxide/potassium Hydroxide from Salt.

Conventionally the salt feed stream needs to be purified by a chelating resin ion exchange step in order to reduce the divalent cation concentration to 0.05–1 ppm. An addition of a chelating agent (such as EDTA) causes a complex of these cations so as to reduce the free calcium ion concentration to substantially less than 1 ppm. Under this mode of operation, a fouling of the cation membranes is no longer a problem and the use of the rather costly ion exchange pretreatment step becomes unnecessary.

DETAILED DESCRIPTION OF THE VARIOUS EMBODIMENTS OF THE INVENTION

In accordance with this invention, the operation of the electrodialysis process employing bipolar membranes is improved through the incorporation or addition of a suitable chelating agent or a combination of chelating agents to the feed stream or to a stream that receives the transported multivalent cations. The salt feed stream may optionally be filtered and purified to remove precipitates, carbon treated to remove higher molecular weight organics that might foul anion membranes and/or nanofiltered to remove multivalent cations.

Chelating agents (such as ethylenediamine tetraacetic acid) are commercially used in food, medical, detergent and other applications for binding with metal ions. An excellent review on the subject can be found in the *Kirk Othmer Encyclopedia of Chemical Technology,* which was cited earlier. In this invention, we are concerned with -the use of sequestering agents, which are agents that combine with metal ions (primarily calcium, magnesium but also with metals such as iron, lanthanum etc.) to produce soluble complexes or chelate compounds with sufficient stability to be formed to an appreciable extent in solution. Usually, the chelating agent is an organic molecule or ion (called a "ligand") that coordinates with a metal ion in more than one position, i.e., through one or more electron donor groups in the ligand. A chelating agent may be bidentate, tridentate, quadridentate etc., depending on whether it has two, three, four or more coordinating groups. The stability of the metal complexes in solution is measured by the magnitude of their formation or stability constant, $K_f$, between the aquo metal ion M and the fully dissociated ligand L:

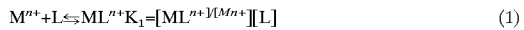

$$M^{n+} + L \rightleftharpoons ML^{n+} \quad K_1 = [ML^{n+}]/[M^{n+}][L] \tag{1}$$

$$ML^{n+} + L \rightleftharpoons ML_2^{n+} \quad K_2 = [ML_2^{n+}]/[ML^{n+}][L] \tag{2}$$

The magnitudes of these equilibrium constants (usually expressed as log K values) are generally taken as measures of solution stability.

The stability of the metal chelate complex depends on the pH of the solution. At low pH values, a competition between the hydrogen and metal ions leads to a breakdown of the metal chelate complex. Conversely, the stability of the complex increases with pH, leading to a progressive reduction in the so called free metal concentration in solution. From (1), we arrive at the expression for the free metal ion concentration [M] as:

$$pM = -\log[M^{n+}] - \log K_1 + \log\{[L]/[ML^{n+}]\} \tag{3}$$

where the term pM, analogous to pH for the hydrogen ion concentration, is a convenient way to express a wide range of free metal ion concentrations in solution ( e.g., pM=7.6 for 1 ppm of free calcium ion in solution). As long as the pH is high enough, the breakdown of the metal chelate buffer is insignificant (for many chelating agents the pH value at which the complex decomposes is in the range of 0 to 2). The free metal ion concentration in solution can be reduced to a very low level by choosing a chelating agent having a high enough formation constant and having an adequate amount of the agent to bind with the metal ion(s). For example, the chelating agent EDTA has a log $K_1$ of 10.59 for $Ca^{2+}$, so that when the solution has an adequate excess of the chelating agent so that the free ligand concentration equals the concentration of the metal chelate ($[L]=[ML^{n+}]$). The free calcium ion concentration in the solution could be $10^{-10.9}$ moles/liter or one part per billion.

The use of chelating agents in bipolar membrane electrodialysis cells has not been considered before. Nevertheless, persons skilled in the art might be able to foresee a number problems in using additives:

The base compartment of the ED cell operates at a high pH; usually 9–14 (the surface of the bipolar membrane is at a pH of ~14). At these pH levels, the metal ions form insoluble hydroxides. As a result, there is competition between the hydroxide ion and the (chelating agent) ligand for the metal ions. The direction of the reaction depends on the relative stability of the metal chelate, its buffer capacity as a function of pH, and the solubility of the metal hydroxide. Most metal hydroxides are highly insoluble at the high pH in the base loop and would, therefore, precipitate and clog the base loop at certain modest levels.

The metal-chelate complex and/or the chelating agent can migrate through the ion exchange membranes, resulting in cross contamination, loss of chelating agent, or otherwise be ineffective in preventing the fouling of the membranes.

Effective removal, recycling and/or destruction of the chelating agent is needed to attain steady state continuous operation I have found that incorporating or adding suitable a chelating agent(s) to certain streams feeding into the electrodialysis cell has surprisingly beneficial effects in terms of improved process reliability and long term operability, reduced operating costs in terms of power consumption and process interruptions, improved membrane life and the avoidance of equipment damage resulting from heating/melting problems. The improvement is particularly applicable to electrodialysis cells employing the bipolar membranes. In many instances, the improvement is such that the additional expenses associated with nanofiltration of feed and/or chelating resin treatments are not needed.

By using an appropriate chelating agent and controlling the pH in the feed loop, the ion exchange membranes used in electrodialysis have been found to be effective in substantially retaining the metal complex within the process loop. The metal ion transport across the cation membrane is small or insignificant enough to avert membrane fouling. When added to the base product loop, the chelating agent was found to be effective in retaining increased amounts of metal ions, especially calcium, in solution so that they are removed with the product base. There is little or no need for frequent acid washing of the base loop. Therefore, in this mode, there is no need for an ion exchange column in communication with the loop. The added chelating agent is removed from the process loop via a purge, and then recycled around the process after breaking the metal-chelate complex and removing the multivalent cations; or the chelating agent could be destroyed during an upstream fermentation step.

Figure 4:
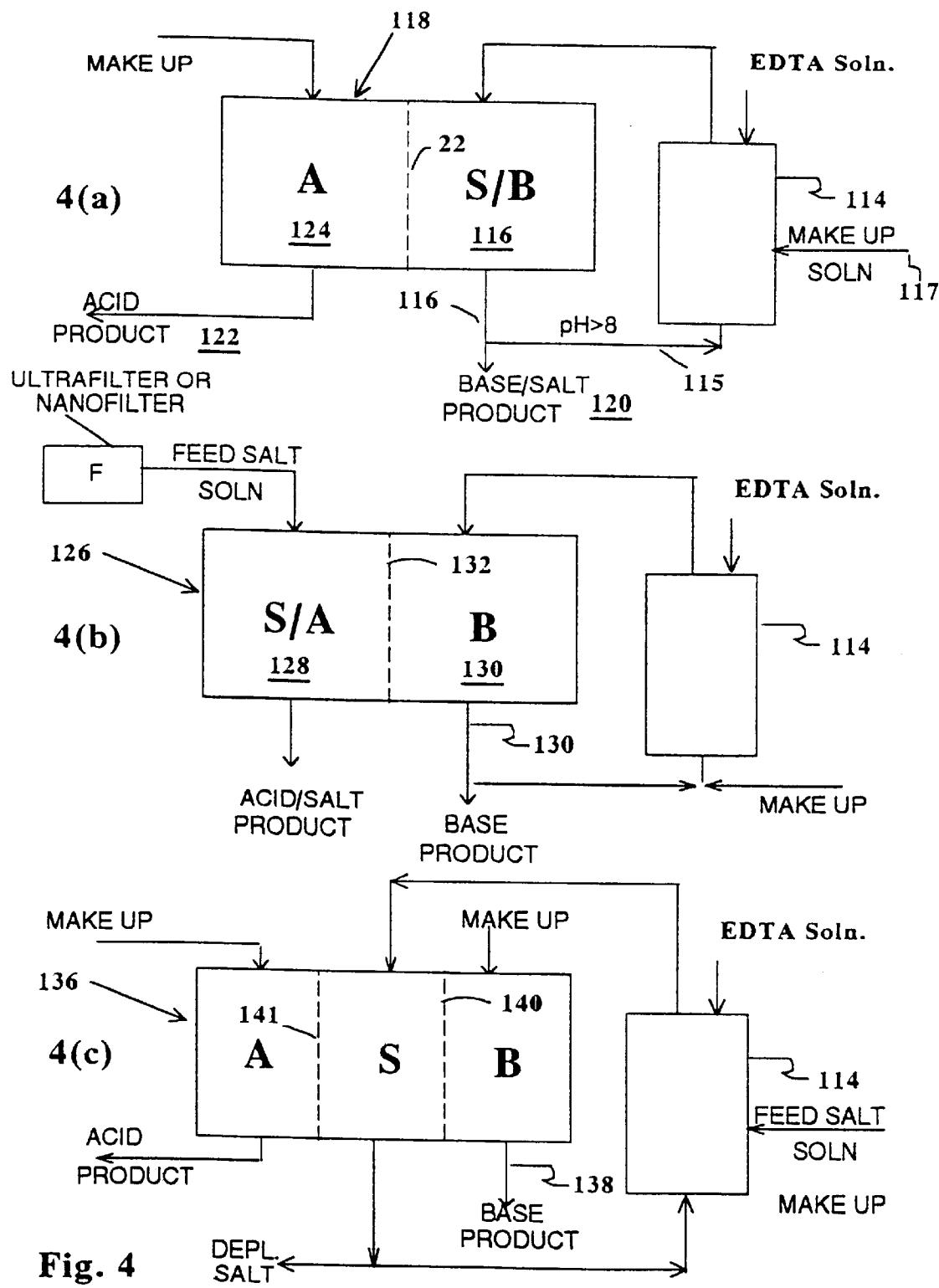
FIGS. 4(a)–4(c) schematically show process configurations illustrating the improved process of this invention.

FIG. 4 shows the basic cell arrangements for the improved processes of this invention. FIG. 4(a) shows a two compartment anion cell 118. Its internal construction is substantially the same as shown in FIG. 1(a). The salt/base compartment S/B is located between the anion selective surface of the bipolar membrane 22 and the adjacent anion membrane 26 (FIG. 4a). A salt solution feed stream is supplied at 117 (FIG. 4a) to the recycle tank 114, wherein the addition of a suitable chelating agent such as EDTA is made. Alternatively, the chelating agent could be a part of the feed solution itself, in which case, the further separate addition of the chelating agent may not be needed. The chelating agent binds with the multivalent cations in the feed salt solution, thereby minimizing or preventing their precipitation within the salt/base loop or on the surface of the bipolar membrane 22.

Under the influence of a direct current driving force anions, e.g. nitrate or lactate, are transported to the acid loop (A), wherein they combine with the hydrogen ions generated by the bipolar membrane 22 to form the acid (nitric acid, lactic acid). Dilution water may be added to the acid loop to control the concentration of the acid generated therein and product acid withdrawn via line 122. Concurrently, the salt feed stream is basified by the hydroxyl ions generated by the bipolar membrane 22 and pH of the feed solution increases. The pH of the solution in the salt/base loop may be maintained in the range of 5–11.5 by the controlled addition of feed solution. The presence or addition of the chelating agent, coupled with pH control of the base loop, mitigates the precipitation of multivalent cations, thereby assuring long term reliable performance of the cell.

FIG. 4(b) shows the operation of a two compartment cation cell 126. Its internal construction is as shown in FIG. 1(b). The feed salt, e.g., sodium bisulfite or ammonium lactate, is supplied to the salt/acid loop, bounded by the cation selective surface of the bipolar membrane 132 and the adjacent cation membrane 42 (FIG. 1(b)). Under the influence of a direct current driving force, the salt is acidified by the protons generated by the bipolar membrane 132, while $NH_4^+$, $Na^+$ and other monovalent cations are transported across the cation membrane 48 (FIG. 1(b)) to the base loop, (B), where they combine with the hydroxyl ions generated by the bipolar membrane 132 to form the base. Concurrently, some of the multivalent cations in the feed stream are also transported to the (B) compartment, wherein they could precipitate out of the feed stream. The addition of a chelating agent EDTA at 114 to the base loop mitigates the problem through the formation of soluble complexes with the multivalent cations. This enables the cell internal area to be essentially free of precipitates The base product containing the multivalent cations in solution is withdrawn from the base loop via the line 130.

The transport of multivalent cations across the cation membranes may be reduced by (a) the use of a monovalent selective cation membrane. Suitable membranes are available from Asahi Glass company and Tokuyama Corporation and/or (b) the use of chelating agents in the acid loop. When processing ammonium lactate, for example, the lactic acid resulting from the acidification of the salt is itself a chelating agent that binds with the multivalent cations in the feed stream, thereby reducing their transport. With salts such as sodium bisulfite or sodium chloride, a deliberate addition of a chelating agent may be made to achieve the same result.

FIG. 4(c) shows the operation of a three compartment cell. Its internal construction is as shown in FIG. 1(c). A salt feed stream, e.g., sodium chloride, along with an added chelating agent such as EDTA is supplied to the salt loop (S), bounded by the cation membrane 48 (FIG. 1(b)) and the anion membrane 50 (FIG. 1(b)), while separate aqueous solutions are supplied to the acid (A) and base (B) loops as shown. Under a direct current driving force, $M^+$ ions (e.g., $Na^+$), are transported across the cation membrane 48 (FIG. 1(b)) to the base loop (B), where they combine with the hydroxyl ions generated by the bipolar membrane to form the base NaOH. The chelating agent in the salt feed stream combines with the multivalent cations in the feed stream, thereby substantially preventing their transport across the cation membrane 48. The fouling of the cation membrane is thereby mitigated, thus enabling a long term trouble-free operation of the cell. As with the two compartment cation cell shown in FIG. 4(b), a suitable chelating agent may also be added to the base loop in order to enhance the solubility of the transported multivalent cations.

Figure 5:
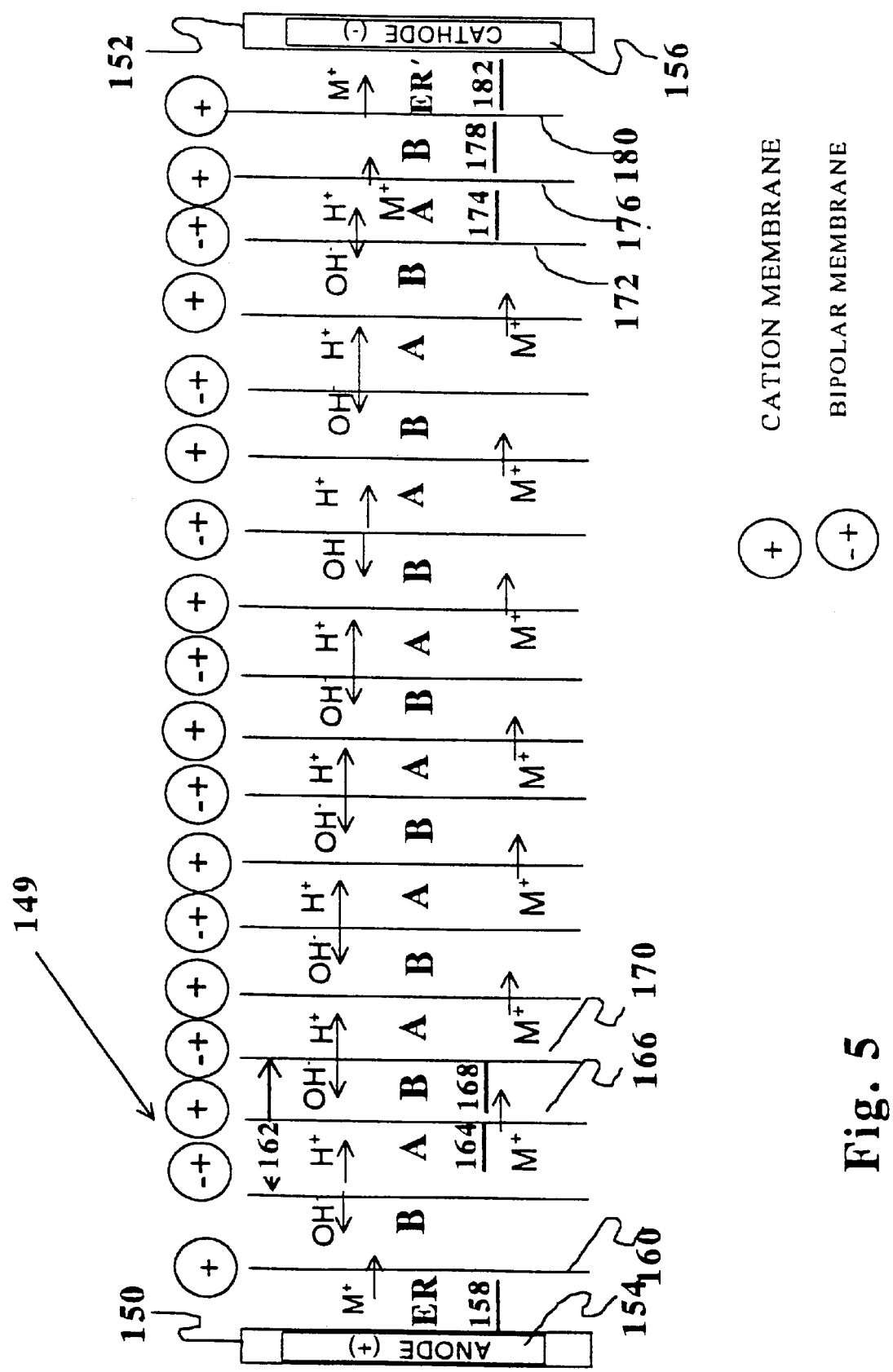
FIG. 5 schematically shows the construction of a two compartment cation cell used to demonstrate the utility of this invention.

The improved processes of this invention are better understood from the following examples. All experiments were carried out using an eight cell, pilot electrodialysis stack that was assembled into two or three compartment configurations. FIG. 5 shows an assembly of the two compartment cation cell 149, which may be used in converting salts of weak acids.

The stack 149 included end plates 150 and 152 to which the electrodes 154, 156 were attached and through which solutions were fed into and removed from the stack. Gaskets 1 mm thick are used to separate the membranes in order to form the solution compartments A and B. Each gasket had an open central area of 465 cm$^2$ (0.5 ft$^2$), through which current can pass. The open central areas are filled with an open meshed screen to keep the membranes separated as well as supported, and to promote a good flow turbulence. Holes punched in the gaskets are aligned to form internal manifolds. Slots (ports) connecting the manifold with the open central area provide a flow of solution into and out of each compartment. My above-mentioned co-pending applications explain all of this in greater detail.

The stack employed a coated metal (platinum) anode 154, supplied by Electrode Products Inc., an electrode rinse compartment ER 158, Sybron Chemicals MC 3475 cation membrane 160, and eight repeating cells. Each cell (for example 162) includes acid compartment A 164, and a CMS (monovalent selective) cation membrane 166 from Tokuyama Corporation. Each cell also includes base compartment B 168 and bipolar membrane 170, available from Aqualytics. The last 172 of the eight bipolar membranes in the stack 149 was followed by an acid compartment A 174, the CMS cation membrane 176, a base compartment B 178, a second MC 3475 cation membrane 180, an electrode rinse compartment ER 182 and a stainless steel cathode 156.

Figure 6:
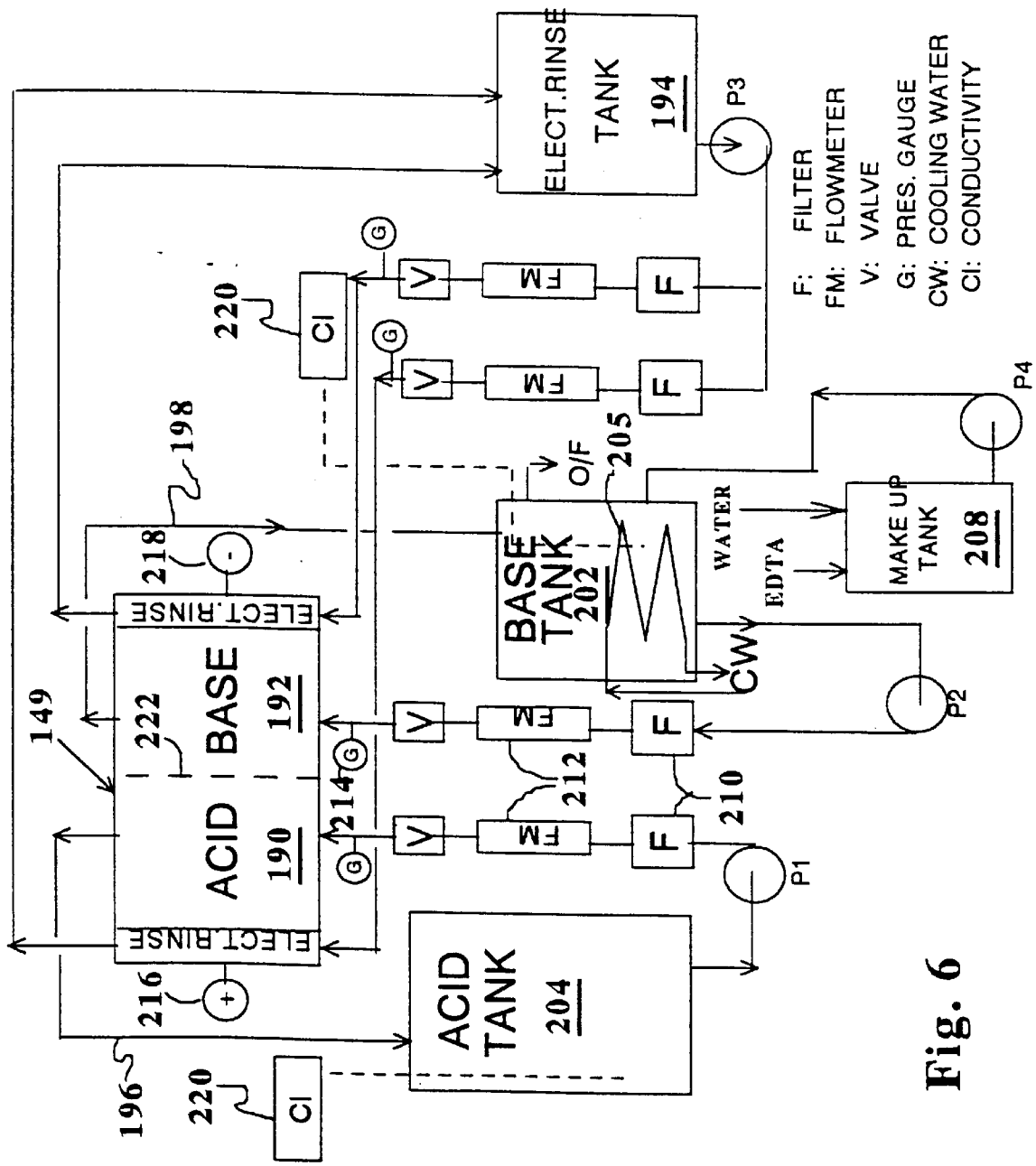
FIG. 6 is a schematic of the pilot system used in testing the improved process.

The assembled stack 149 was placed in the system shown schematically in FIG. 6 in order to carry out the electrodialysis experiments. Three pumps (P1–P3) were used to circulate solutions to the acid (190), base (192) and electrode rinse (194) compartments from their respective recycle tanks 204, 202, 194 at a rate of 2.5–4 l/min. The acid loop was operated in a batch mode, while the base loop 198 was run in a feed and bleed mode. During operation, a pump P4 may add fresh water, or a salt, or an acidic solution, or a solution containing a chelating agent (e.g. EDTA) via a make up tank 208, as needed. Each of the base and the electrode rinse tanks 202, 194 have a nominal volume of 5 liters. The acid recycle tank 204 had a capacity for processing as much as 180 liters, per batch. A cooling water coil 205 in the base tank 202 controls the temperature.

Cartridge filters 210, flow meters 212 and pressure gauges 214 were used in each loop to ensure a flow of clear fluids at known flow rates and pressure drops in the three loops. A separate pump (not shown) was used to supply the feed salt solution to acid recycle tank 204. A DC power supply (not shown) was connected to the anode and cathode terminals 216, 218 of the stack. The requisite controllers for providing and controlling the electrical current input and voltage are located in the power supply itself. Conductivity meters 220 were used in the acid and base loops in order to monitor the progress of the electrodialysis operation.

The system was initially charged with the requisite quantity of the filtered salt solution which was fed into the acid tank 204. A dilute alkaline solution along with a small amount of salt solution was added to the base tank 202 to provide the requisite conductivity, at start up. Dilute ammonium sulfate solution was used in the electrode rinse tank 194. Subsequently, water or an aqueous solution containing ~0.2 wt % sulfuric acid and ~800 ppm EDTA (as sodium salt) was added at a constant rate to the base loop from tank 208 via pump P4. The electrode rinse tank was filled with ~10 wt % ammonium sulfate (for ammonium salt conversion application) solution.

Recirculating pumps P1–P3 were started and the flow rates adjusted in order to get an inlet pressure of ~6 psi in each of the loops. The DC current was applied and the amperage adjusted to obtain 42.5–45 A (85–90 A/ft$^2$ current density). As the batch progressed, the conductivity of the loop decreased due to the transport of the monovalent cation ($NH_4^+$, $K^+$, $Na^+$) across the cation membranes 222, with a concurrent formation of the acid in the acid loop. Consequently the cell voltage increased as the batch processing progressed.

The batch was deemed complete when a target acid conductivity, usually <10 mS/cm, is reached. In the base compartment(s) 192, the monovalent cations combine with $OH^-$ ions to form the base product. For most experiments, electrical conductivity in the base loop was maintained at >10 mS/cm by an addition of the dilute sulfuric solution.

Comparative Example 1

A test was carried out on the conversion of ammonium-2ketogulonic acid ($NH_4$-2KLG) to the free acid 2ketogulonic acid (2KLG). The pilot cell had eight cells as shown in FIG. 5, but used a ruthenium oxide coated anode, an acid compartment next to the first MC 3475 cation membrane 160 and a cation membrane adjacent to the first base compartment. At the other end, the seventh bipolar membrane was followed by an acid compartment, a cation membrane, a base compartment, and an eighth bipolar membrane adjacent the cathode rinse loop ER' in place of the second MC 34745 cation membrane 180. Both the AQ cation and bipolar membranes were made by Aqualytics, and were used in this test. About 10 wt % sulfuric acid was used in the electrode rinse loops.

The starting solution was obtained by neutralizing a fermentation derived sample of 2KLG with ammonia and contained 170 gm/l 2KLG and 12.99 gm/l $NH_3$ equivalents, at a pH of about 9. Twenty eight liters of the feed stream was processed in the electrodialysis cell using the set up shown in FIG. 6. The conductivity decreased from 35.1 mS/cm to 8.6 mS/cm due to acidification and the concurrent transport of ammonia out of the feed loop 190. A sodium chloride solution from tank 208 was added to the base loop 192 via tank 202, in order to maintain a conductivity therein of 16–20 mS/cm. Dilute sulfuric acid was used in the electrode rinse loop. During the trial, samples of the feed loop were analyzed periodically. The results were as shown on the following Table 1. The slight increase in conductivity after the start is due to solution heating.

TABLE 1

| Run Time min. | Voltage V | Current A | Acid Conductivity mS/cm | Acid Volume L | Acid loop analysis ||||
|---|---|---|---|---|---|---|---|---|---|
| | | | | | 2KLG gm/l | pH | $NH_3$ gm/l | Ca ppm | Mg ppm |
| 0 | 0 | 0 | 35.1 | 28 | 170 | 9.1 | 12.99 | 21.9 | 5.62 |
| 6 | 38 | 34 | 35.4 | | | | | | |
| 11 | 35.1 | 40 | 38.2 | | 175 | 8.6 | 11.17 | 20.3 | 4.86 |
| 21 | 32.7 | 40 | 35.1 | | | | | | |
| 27 | 32.3 | 40 | 38 | ~28 | 174 | 4.74 | 10.61 | 19 | 4.52 |
| 33 | 32.3 | 40 | 34.4 | | | | | | |
| 85 | 34.1 | 40 | 28 | 27.5 | 178 | 3.32 | 6.0 | 16.3 | 3.44 |
| 118 | 46.6 | 40 | 23.1 | | 180 | | 4.33 | 13.2 | 2.67 |
| 125 | 34.2 | 40 | 22.2 | | | | | | |
| 143 | 34.9 | 40 | 19.2 | 26.5 | 181 | 2.73 | 3.35 | 10.4 | 2.04 |
| 211 | 38.1 | 40 | 11.5 | ~26 | 186 | 2.12 | 1.40 | 3.36 | 0.63 |
| 255 | 38.1 | 38.2 | 9.5 | 25.5 | 189 | 2.01 | 0.84 | 1.28 | 0.23 |
| 283 | 38.1 | 37.9 | 8.6 | | 190 | | 0.73 | 0.59 | 0.13 |

The final acid product contained 190 gm/l 2KLG and only 730 ppm $NH_3$ representing 95% removal of ammonium cations from the salt. The current efficiency (the ratio of the equivalents of ammonium ions transported to the faradays of current input).was about 40%. It can be seen that substantially all of the calcium and magnesium values in the salt feed stream have also been transported across the AQ cation membranes such as 160, 166. This is apparently because 2KLG is a relatively strong acid with little or no chelating ability for the divalent cations. Additionally, the AQ cations, being of a non-selective type, enable a ready transport of the monovalent as well as the multivalent cations. These multivalent cations tend to precipitate in the base loop and adversely impact the long term operability of the cell in time, unless certain pH concentration and flow parameters are maintained therein.

Solubility Data for Divalent Ions as a Function of pH

Thirty seven batches of ammonium and sodium lactate and one with $NH_4$–2KLG feed streams were processed in the pilot cell used in the above Comparative Example, with the processing of each batch lasting from 6 to>24 hours. The lactate were feed streams taken from a fermentation of dextrose. The 2KLG feed stream was obtained by neutralizing the acid with ammonia. Each of the feed streams was subjected to simple filtration or to ultrafiltration prior to processing in the electrodialysis cell. The feed sreams had 20–150 ppm Ca and 6–60 ppm Mg.

When processing the sodium lactate salt, the pH of the sodium alkali base product was limited by the addition of gaseous $CO_2$. CMV, CMT (from Asahi Glass Company); or, or AQ cation membranes were used in these batch trials. The CMV membrane was used in the first eighteen and the CMT membrane in the later nineteen lactate tests. The CMT, CMV cation membranes were in excellent condition after the process tests, with no evidence of fouling by multivalent cations in the feed streams. The AQ cations, used in the 2KLG production process described in the Comparative Example above were whitish, indicating calcium fouling. Samples of the product base were analyzed for both their divalent metals content and pH. The solutions were clear so that the measured concentrations of these ions represent their solubility in the base loop.

Figure 7:
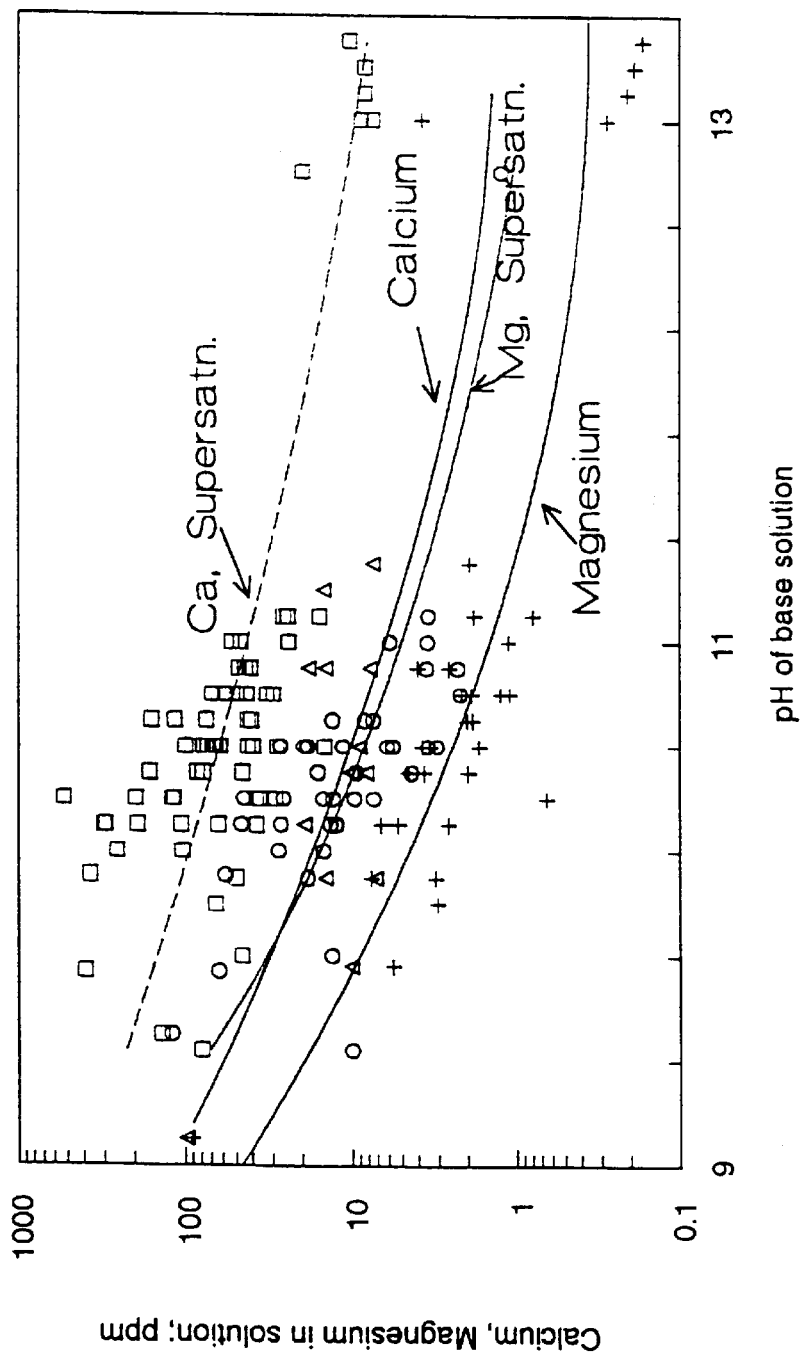
FIG. 7 is a graph summarizing solubility data for calcium and magnesium, as a function of a base solution pH.

The results of the study on solubility as a function of pH are plotted in FIG. 7. When producing ammoniacal solutions, the pH ranged from 9 to about 11.4. While the sodium alkali solutions had pH range of about 12 to 13.4. The data could be divided into two sections for each of calcium and magnesium. One set of data represents the solubility limit, while the second set of data represents a supersaturated state where the alkaline solution can hold significantly higher levels of the divalent metals. However, there is always the potential for spontaneous precipitation and the consequent plugging of the base loop of the electrodialysis cell.

Consequently, for a reliable operation of the cell, one has to maintain the calcium and magnesium concentrations at or below their solubility limit. For example, at a pH of 11, which is the pH in the base loop for ammonia production, the solubility for Ca and Mg are ~10 ppm and ~2 ppm respectively. Since the surface of the bipolar membrane is at a high pH (~14), even lower concentrations would be desirable via an adequate dilution or buffering (e.g. at a lower pH) in order to assure long term trouble-free operation of the cell.

EXAMPLE 1

Seventeen batches were carried out with an ammonium lactate conversion by using the pilot cell shown in FIG. 5 and the process set up shown in FIG. 6. Ammonium lactate obtained via fermentation was ultrafiltered prior to feeding it to the acid recycle tank 204 (FIG. 6). The ammonium lactate contained ~60 gm/l of lactic as lactate at a pH of ~5 and a conductivity of ~45 mS/cm. The salt feed stream had ~52 ppm Ca and 42 ppm Mg. For batches 15–17, additional calcium was added to the feed stream so that the starting calcium level was ~70 ppm. Depending on the size of the batch, the run time per batch varied from 7.3 to 16.5 hours. During the processing of each batch, 10 ml/min of an aqueous solution containing ~2700 ppm sulfuric acid ~1000 ppm EDTA (as tetra sodium salt) was added to the ammonia product loop in order to provide, respectively, a minimum conductivity (10–12 mS/cm) in the loop and to determine whether the retention of the multivalent cations in solution can be increased. The solubility of EDTA, particularly in the acidic solution is rather limited (<500 ppm). The actual EDTA content in a typical feed solution to the ammonia product loop was 380 ppm. The batches were run at a constant current of 42.5–45 A.

The seventeen batches were run back to back, in order to fully assess the impact of the chelating agent in enhancing the retention of the multivalent cations. Recycle rates in the various loops remained stable during the various batches, thus indicating that there were no significant precipitation or plugging problems. Ammonia removal per batch averaged 83.6%. The conductivity of the acid product at the conclusion of each batch was usually <10 mS/cm. Samples of the acid and base products were drawn periodically during each batch run and analyzed for ammonia, lactic and metals. The seventeen processing batches lasted a total of ~200 hours.

The results are summarized in Table 1. It can be seen that the cell voltage at the conclusion of each batch had been fairly constant, indicating that the membranes or the cell internals were not being fouled. The overall retention of calcium and magnesium within the acid loop, as shown in the last two columns, is high, averaging >95% and >99% respectively. The chelating ability of lactic acid, coupled with the monovalent ion selectivity of the CMS cations are doubtless responsible for this overall retention, which in turn reduces the amount and concentration of these metals in the ammonia product loop. Nevertheless, a material balance shows that, in the absence of any precipitation, the theoretical (calculated) concentration of calcium in the ammonia loop, would be 15–30 ppm (Column 9 in Table 1), which exceeds the solubility by 50–200% and would, therefore, cause long term operational problems.

Column 9 in Table 1 shows the average concentrations of calcium for each batch, the overall average being 22.9 ppm. The actual values measured during different phases of the batch processing were in the range of 15 to 36 ppm. for calcium and 0.5–6 ppm for magnesium.

All of these figures are substantially greater than they would be in the absence of the chelating agent as shown in FIG. 6. The addition of EDTA to the ammonia loop thus enhanced the retention of the divalent metals by 100–260% and allowed a long term operation of the cell in a reproducible manner. The retention of the divalent cations in the solution can be increased further by adding higher quantities of a different, more soluble chelating agent. One can also add a larger amount of EDTA directly to the ammonia loop, thereby circumventing the solubility limitations encountered in this example.

Comparative Example 2

A long term trial on the conversion of sodium chloride to NaOH and acid was carried out in an 8 cell pilot unit of the type shown in FIG. 5. The cell was constructed as a three compartment unit and contained AQ bipolar membranes, AQ-PS cation membranes made by Aqualytics and AHA-2 anion membranes made by Tokuyama Corporation. There were 27 compartments in all, comprising eight sets of base, salt, acid, compartments with an extra base compartment at the end and the two electrode rinse compartments. The anode was made of nickel and the cathode was made of stainless steel. A liquid with ~10 wt % NaOH was circulated in the electrode rinse compartments.

The assembled cell was placed in a process test unit modified from that shown on FIG. 6. The acid tank 204 was converted into a salt solution storage tank. Two 5 liter recycle tanks along with the re-circulation loops containing pumps, flow meters, pressure gauges and valves were added for the salt and acid loops. For the NaCl conversion process, the salt, base and acid loops were run in a feed and bleed mode. Make up salt from the salt holding tank 204 was added to the salt recycle tank under a conductivity control. De-ionized water was metered into the base recycle tank so as to achieve a caustic soda concentration of ~3N (120 gm/l). The HCl generated in the acid loop was partially neutralized by an addition of a metered amount of lysine taken from a storage tank via a metering pump, and was withdrawn at a steady overflow rate from the acid recycle tank. The process was run at a steady current input of 50 A (100 A/ft$^2$ current density).

The salt feed stream for the process was prepared by dissolving 98+% purity NaCl (supplied by G. S. Robbins). Sodium carbonate and sodium hydroxide were added to elevate the pH of the salt solution to ~9–10.5. The feed stream was then subjected to nanofiltration using DK-5 nano-filters from Desal (Desalination Systems, a unit of Osmonics Inc.). The DK-5 elements have a nominal molecular weight cut off of ~200 Daltons and are known to have substantial rejection for multivalent cations. In actual trials, the nanofiltration step yielded a clear salt solution that had no detectable magnesium, but contained 0–15 ppm calcium.

In the electrodialysis, 80–85% of the sodium chloride in the feed stream was converted to caustic soda and hydrochloric acid in the base and acid loops, respectively. A certain amount of water is also transported to the acid and base loops as water of hydration. The depleted salt solution, contained 15–20% of the salt in the feed solution and usually was 30–50% of the feed volume. This depleted salt solution overflowed out of the salt recycle tank and was sent to waste. The selectivity of the cation and anion membranes in this process was such that the depleted salt solution from the process was alkaline and contained 3–10 gm/l of free NaOH and had a pH of 13–14.

An initial study, lasting ~310 hours was carried out by using the nano-filtered salt feed stream, as described above. Salt feed and the overflow rates were measured or calculated via a material balance at frequent intervals. Samples of the salt feed and overflow were also analyzed for their calcium content. From the results of this study, the retention, transport, or loss of calcium in the salt loop was calculated. The results are set forth in Table 2 and were as follows:

TABLE 2

| Time, | Salt Feed into Cell, ppm/wt | | Salt Overflow, ppm/wt | | Calcium Retention |
|---|---|---|---|---|---|
| Hours | Sodium | Calcium | Sodium | Calcium | in Salt Loop, % |
| 16.7 | 35700 | 5.56 | 8680 | 1.56 | 15 |
| 27.6 | 52100 | 3.02 | 13100 | 1.18 | 21 |
| 90 | 53100 | 1.1 | 16700 | 0 | 0 |
| 150 | 64800 | 1.19 | 26000 | 0.4 | 18 |
| 213 | 68500 | 1.24 | 34200 | 0.52 | 22 |
| 274 | 64400 | 0.95 | 29700 | 0.55 | 30 |
| 313 | 59900 | 0.96 | 16600 | 0.31 | 17 |

In terms of percentage, the amount of calcium retained in the salt loop is roughly the same as the unconverted sodium chloride, indicating that both sodium and calcium are being transported relatively easily and in the approximately same proportion across the cation membrane and into the base loop. The solubility of calcium in the ~3N NaOH solution in the base loop is 0–0.5 ppm, so that the transported calcium will likely precipitate out within the cation membrane and cause fouling problems in the long term.

EXAMPLE 2

The long term trial on sodium chloride conversion was continued in two phases in order to determine the impact of a chelating agent addition on the retention of calcium in the salt loop. The salt conversion to caustic soda and hydrochloric acid was once again in the 80–85% range as with the Comparative Example 2. In the first phase, the chelating agent EDTA was added to the sodium chloride solution prior to the nanofiltration step, with the expectation that the large size Ca-EDTA complex, which is larger than the nominal molecular size cutoff of the nanofilter, can be filtered out, thus yielding a relatively calcium free sodium chloride solution for feeding the ED cell. It turned out that the nanofilter was surprisingly ineffective in removing the complex, resulting in rather high levels of calcium in the salt feed steam to the ED cell. Therefore, in the second phase the EDTA was added to the salt solution that had been pH adjusted and nanofiltered, as described in the Comparative Example above. Both purified salt and commercial rock salt were used in preparing the nanofiltered solutions in the second phase. The EDTA concentration (added in the form of $K_2$EDTA) in the salt feed stream to the ED cell was ~160 ppm in phase I and ~70 ppm in phase II.

As with the earlier Comparative Example, the salt feed stream and the overflow rates were measured or calculated via a material balance at frequent intervals. Samples of the salt feed stream and overflow were analyzed for their calcium content. From this analysis, the retention, transport, or loss of calcium in the salt loop was calculated. The hours of operation are cumulative with the Comparative Example 2. The results are set forth on Table 3, as follows.

Phase I: EDTA addition to salt solution prior to nanofiltration. Higher Calcium in feed solution

TABLE 3

| Time, | Salt Feed into Cell, ppm/wt | | Salt Overflow, ppm/wt | | Calcium Retention |
|---|---|---|---|---|---|
| Hours | Sodium | Calcium | Sodium | Calcium | in Salt Loop, % |
| 324 | 65100 | 11.2 | 33800 | 19.8 | 102 |
| 348 | 64800 | 15.7 | 31500 | 30.3 | 105 |
| 374 | 65300 | 16.7 | 29900 | 33.1 | 100 |
| 392 | 63000 | 15.5 | 24000 | 30.4 | 106 |
| 418 | 58900 | 22.7 | 31900 | 36.5 | 91 |

Phase II: EDTA addition to salt solution after nanofiltration. High purity salt used.

TABLE 4

| Time, | Salt Feed into Cell, ppm/wt | | Salt Overflow, ppm/wt | | Calcium Retention |
|---|---|---|---|---|---|
| Hours | Sodium | Calcium | Sodium | Calcium | in Salt Loop, % |
| 443 | 60400 | 9.55 | 3600 | 17.6 | 98 |
| 478 | 72800 | 4.23 | 32400 | 9.55 | 106 |
| 502 | 74800 | 4.13 | 31000 | 9.79 | 98 |
| 520 | 70000 | 4.28 | 29500 | 8.72 | 94 |
| 544 | 69000 | 2.89 | 27100 | 6.69 | 94 |
| 570 | 69400 | 2.94 | 30900 | 6.29 | 96 |
| 640 | 70600 | 4.27 | 30700 | 9.19 | ~100 |
| 736 | 83300 | 1.9 | 33100 | 6.09 | ~100 |
| 761 | 77000 | 2.71 | 31300 | 6.63 | ~100 |

Phase II: EDTA addition to salt solution after nanofiltration. Commercial rock salt used.

TABLE 5

| Time, | Salt Feed into Cell, ppm/wt | | Salt Overflow, ppm/wt | | Calcium Retention |
|---|---|---|---|---|---|
| Hours | Sodium | Calcium | Sodium | Calcium | in Salt Loop, % |
| 780 | 85800 | 5.48 | 33000 | 19.3 | 100 |
| 802 | 89400 | 5.64 | 30800 | 20 | 100 |

TABLE 5-continued

| Time, | Salt Feed into Cell, ppm/wt | | Salt Overflow, ppm/wt | | Calcium Retention |
|---|---|---|---|---|---|
| Hours | Sodium | Calcium | Sodium | Calcium | in Salt Loop, % |
| 832 | 82000 | 11.4 | 31800 | 35.7 | 97 |
| 880 | 74900 | 4.26 | 36000 | 9.77 | 103 |
| 904 | 81700 | 2.99 | 36500 | 7.34 | 113 |
| 929 | 79600 | 2.86 | 32200 | 7.68 | 112 |
| 976 | 79300 | 15.7 | 35600 | 36.5 | 103 |
| 1000 | 79300 | 15.7 | 35600 | 36.5 | 103 |

It can be seen that, despite the high level of sodium chloride conversion in the process, the addition of EDTA results in about 100% retention of calcium within the salt loop. In the absence of the chelating agent in the Comparative Example above, the calcium retention was only 0–30%. Consequently, the use of a chelating agent to bind up the calcium and thereby inhibit its transport across the cation membranes is highly effective in the ED process. It is believed that, unlike the nanofilter, the pores in the ion exchange membranes in the ED cell are considerably smaller and the membranes are, therefore, able to retain the Ca-EDTA complex within the salt loop. In addition, the absence of oxidation/reduction reactions in the ED cell enables the chelating agent to remain chemically stable so that it can effectively perform its chelating function.

Process Applications

The above example illustrates the utility of the added chelating agent in retaining the multivalent cations within the salt loop of a three compartment cell. Therefore, in salt splitting applications to make an acid and base, (e.g., sodium chloride), sulfate processing, one does not have to use a chelating resin pretreatment. However, it would be preferable to utilize the pH adjustment filtration step as employed in the Examples above, so that sparingly soluble metals (such as Fe and Mg) are removed upstream of the ED cell and that the chelating agent requirement is kept as small as practical.

A number of other electrodialysis processes can also be improved through the use of chelating agents to control the concentration of multivalent cations and their transport into or out of specific process loops.

Recovery of Organic Acids

A number of organic acids, (e.g. lactic, acetic, succinic), are produced in the form of salts via fermentation. FIG. 8 shows a process using the improvement disclosed herein. One or more fermenters 300 may be operated in a batch mode to produce the organic acid in its salt form. For optimum productivity, the fermentation is conducted at a pH of about 4–7. The pH is maintained through an addition of an alkali. Ammonia is a preferred alkali because of its low cost and the ease of its recovery in a downstream electrodialysis operation.

The product organic salt is filtered at 302 to remove any insoluble cell mass. Subsequently, the salt is ultrafiltered at 304 to remove any finely suspended solids. The clear filtrate is then optionally evaporated at 306 and carbon treated at 308 prior to processing in the two compartment cation electrodialysis cell 310. The evaporation step stabilizes the feed stream by preventing microbial growth during storage and processing. It also provides a higher removal of ammonia in the electrodialysis operation. Carbon treatment of the feed stream removes higher molecular weight organics that might otherwise foul the membranes. The concentrated, purified feed stream is fed to the acid recycle tank 312 of the electrodialysis cells.

One or more electrodialysis process units, each containing 150–200 or more cells may be employed at 310 in the conversion of the ammonium salt to the organic acid and ammonia. The electrodialysis cell is of the type shown in FIG. 1(b), 2(a) or 3. The acid loop 314 is operated in a batch mode, with the product acid being pumped out of the acid recycle tank 312 when the target conversion is reached. A fresh batch is then added to the acid recycle tank and the process is continued.

Ammonium hydroxide is generated in the base loop 316 of the ED cells. The base loop may be operated in either a preferred steady state feed and bleed mode or in a batch mode. Dilution water and a small amount of acid/salt may be added to the base loop 316, if necessary, in order to maintain the product ammonia concentration and conductivity at certain target levels, usually 50–100 gm/l, and >15 mS/cm, respectively. An aqueous solution of a chelating agent such as EDTA is metered, preferably directly, into the ammonia recycle tank 318 in order to help keep any multivalent cations in solution within the base loop.

A three compartment cell such as shown in FIG. 1(c) or 2(b) may be used in place of the two compartment cation cell for producing higher purity acids or processing salts of stronger acids.

A concentrated ammonium hydroxide solution is generated in the base loop 316. This, along with the added chelating agent as well as the multivalent cations is recycled to the fermenter 300 for pH adjustment.

Product acid from the acid recycle tank 312 may be further treated via an ion exchange to remove residual cations ($NH_3$, Na, Ca, etc.) and anions (Cl, $SO_4$) and to forward the resulting fluids to a final distillation/purification step. However, I have found that when processing an acid such as lactic, a significant amount (such as 2–5%), is tied with the ion exchange resins due to chelation or co- absorption. This acid, which is eluted with the contaminating ions during the regeneration step, represents a significant loss.

FIG. 8 also shows a process improvement for purification of the acid using a desalting electrodialysis (D-ED) step. The D-ED cell 320 is a two compartment ED unit, similar to the ED cell shown in FIG. 4, except that it comprises alternating cation and anion exchange membranes which, in turn, form alternating diluting (D) and concentrating (C) compartments. The acid to be purified (i.e. product acid from the acid recycle tank) is circulated in a set of desalting compartments (D) within the unit 320, while a liquid comprising water is circulated in the adjacent concentration compartments (C). Under a direct current driving force, the cationic and anionic contaminants, along with a small portion organic acid are transported to the C compartments. This concentrate stream is preferably returned to the fermenter 300. A small portion of the concentrate product may be purged to avoid a build up of undesirable anions, such as chlorides. In this manner, the loss of the organic acid is reduced or eliminated. The use of desalting electrodialysis for purifying organic acids can be better understood from the following Example.

EXAMPLE 3

A desalting ED cell was constructed in a manner shown in FIG. 5. The 8-cell unit used CM-1 cation membranes and AMX anion membranes, both from Tokuyama Corporation. The test used a ruthenium oxide coated anode 154, an electrode rinse compartment ER isolated with a CMT cation membrane 160 from Asahi Glass, eight sets of C and D compartments 320 separated by AMX, CM-1 membranes, an additional C compartment, a second CMT cation membrane 180, a electrode rinse compartment ER' and a stainless steel cathode 156.

The assembled cell was placed in a process test unit similar to that shown in FIG. 6. Here, the acid 204 and base 202 tanks are more properly designated dilute and concentrate tanks. A dilute sulfuric acid solution was placed in the concentrate tank and electrode rinse tanks. The dilute tank was charged with 18.8 liters of a lactic acid solution containing 332 gm/l of lactic, 5.29 gm/l $NH_3$, 368 ppm Na, 768 ppm K, 136 ppm Ca, 631 ppm Mg, 32 ppm Fe, 393 ppm P, 690 ppm Cl and ~3200 S. ~85 ml of concentrated sulfuric acid was added to the dilute tank so that at least a portion of the ammonium lactate will be converted to free lactic acid and ammonium sulfate. The free lactic is relatively un-dissociated and, therefore, will not be not readily transport across the ion exchange membranes.

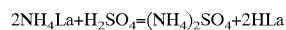

$$2NH_4La+H_2SO_4=(NH_4)_2SO_4+2HLa$$

The added acid increased the sulfur content in the lactic feed to 5770 ppm. The conductivity of the feed stream after the sulfuric addition was 12.66 mS/cm. Recycle pumps P1–P3 were started and the fluid flow streams in the various loop were set at 2–4 l/min and at an inlet pressure of 5–6 psi. The DC power was turned on and the cell operated at a current input of 14A (28A/ft² current density). As the desalting of the lactic feed stream progressed, the overall cell voltage increased from ~12V to 26V while the conductivity decreased due to the transport of the various cations and anions. The experiment was stopped after 4.25 hours when the conductivity of the feed had reached 2.79 mS/cm.

Eighteen liters of product acid was obtained from the trial, and contained 334 gm/l lactic, ~90 ppm $NH_3$, 2.4 ppm Na, 10 ppm K, 6.4 ppm Ca, 35 ppm Mg 2 ppm Fe, 29 ppm P, 14 ppm S and 23 ppm Cl. An overall removal of the contaminating ions was 95–99.9%, while the lactic loss to the concentrate loop was ~4%.

The concentrate stream contains the transported lactic as well as ammonium, Ca and Mg and is recycled to the fermenter. In this manner, the loss of lactic from the process is avoided.

Continuous Fermentation/Recovery of Organic Acids

FIG. 8(a) shows the use of this invention in a continuous process for the production of an organic acid, such as lactic acid. A substrate, such as dextrose, is fermented at 330 to yield lactic acid that is recovered as ammonium lactate. A steady stream of this lactate solution is ultrafiltered at 332 and the insoluble material (such as cells), are returned to the fermenter. The filtered lactate solution is then processed in the salt/base compartment (S/B) of a two compartment anion cell 334 which is similar to the cell such as in FIG. 1(a). A small amount of a chelating agent, such as EDTA, is also added at 336 to the feed lactate solution in order to help retain the calcium/magnesium values in solution. The addition of the chelating agent enables the ED process base loop to operate at a much higher pH, ~11. This, in turn, would drastically reduce the recycle loop volume.

In the ED cell, the feed lactate is basified by the application of a direct current driving force, thus liberating a portion of the ammonium values as the free base. Concurrently, lactate anions are transported to the acid loop (A) where they combine with the $H^+$ ions generated by the bipolar membrane to form lactic acid. The product lactic is withdrawn at 338 as a concentrated solution from the acid loop.

Recovery of Sulfur Dioxide from Flue Gas Scrubbing

FIG. 9 shows the application of this invention in the recovery of sulfur dioxide from flue gas scrubbing operations. An aqueous solution of an active alkali (such as sodium sulfite) is used to absorb $SO_2$ from flue gases, resulting in the formation of the bisulfite. The active alkali solution will also contain the chelating agent. During the process, a portion of the sulfite is oxidized by the oxygen in the flue gas, resulting in the formation of byproduct sulfate. The reactions are:

$Na_2SO_3+SO_2+H_2O=2NaHSO_3$ $Na_2SO_3+½O_2=Na_2S_4$

The presence in the feed sulfite solution of a chelating agent (such as citric acid or EDTA) which is added during the downstream $SO_2$ recovery step might also reduce the extent of sulfate formation. In the absorber, the conversion of the sulfite to bisulfite causes the pH of the solution to decrease from about 9 to about 4–5.

In greater detail, the bisulfite rich solution from the absorber 340 is divided into two parts and fed to the base (B) and the salt/acid (S/A) compartments, respectively, of a two compartment cation cell 342, as shown. The feed to the base loop is preferably recycled and mixed with the higher pH at 344 from the cell and filtered at 346 to remove any insoluble material (e.g. Ca, Mg salts). A make-up chelating agent is added at tank 348 to the filtered solution and then fed to the base loop of the cell 342. The chelating agent allows higher levels of the multivalent cations to be in solution and thus to enable long term trouble-free operation of the ED cell.

Under a direct current driving force the feed bisulfite is acidified by the protons generated at the bipolar membranes in the S/A loop resulting in the formation of sulfurous acid. The sulfurous acid readily decomposes to yield sulfur dioxide. Concurrently, sodium cations are transported from the S/A loop across the cation membrane 350 to the B loop, where they combine with the bisulfite in the feed stream and the hydroxyl ions generated by the bipolar membrane to form the sulfite. Any excess of hydroxide and sodium ions will result in the formation of NaOH and a further increase in the pH of the base product solution. The reactions are:

| Salt/Acid loop: | $NaHSO_3 + H^+ - Na^- = H_2SO_3$ |
| --- | --- |
| | $H_2SO_3 = H_2O + SO_2$ |
| Base loop | $NaHSO_3 + Na^+ + OH^- = Na_2SO_3 + H_2O$ |
| | $Na^+ + OH^- = NaOH$ |

The regenerated alkali is returned to the absorber 340. The $SO_2$ rich solution from the salt/acid loop is forwarded to a stripper 352, where $SO_2$ is recovered by the use of steam or a vacuum. A portion of the solution after the $SO_2$ stripping is purged to avoid sulfate (and multivalent metals) build up, while the rest of the solution is returned the absorber in order maintain the proper water balance. The loss of the chelating agent can be kept small, for example, by cooling the purge solution to remove the solid sulfate, while the liquor containing the chelating agent is recycled to the absorber.

Flue Gas Scrubbing with an Organic Salt Solution and $SO_2$ Recovery

The chelating and buffering ability of organic acids can be used in a novel ED process for recovery of $SO_2$. FIG. 10 shows a process that uses a citrate salt solution to absorb $SO_2$ from a flue gas and uses a two compartment anion cell 366 to recover the $SO_2$ in a concentrated form. The basics of citrate scrubbing are fully described in literature, a particularly good reference being SRI Report No: 63B, Part II, 221–253 (1980). The chemistry of $SO_2$ absorption is essentially the same as described above, except that the presence of citrate ion depresses the pH of the solution to 3.5–4.5 range and helps reduce sulfate formation to the 1–2% range vs. the 5–10% when the scrubbing is with only the sodium alkali. The lower pH also increases the relative amount of monovalent bisulfite $HSO_3^-$ over the sulfite $SO_3^=$ which is a useful feature for the downstream ED recovery step. The lower pH also allows a cleaner operation by eliminating scale formation (i.e. precipitation of Ca, Mg salts) in the scrubber internals.

The absorber 368 product solution containing the bisulfite is filtered at 371 to remove any insoluble matter and fed to the salt/base (S/B) loop of the two compartment anion cell via tank 372, while a stream comprising water is fed to the acid loop. The cell 366 is construction as shown in FIG. 1(b) and uses bipolar and (preferably) monovalent selective anion membranes. The use of monovalent membrane such as ACS from Tokuyama Soda will provide a preferential removal of the bisulfite anion over the divalent sulfite anion.

Under a direct current driving force, a portion of the bisulfite anions and some of the sulfite and sulfate anions are transported to the acid loop a where they combine with the protons generated by the bipolar membrane 370 to form sulfurous acid/sulfuric acid. Simultaneously, the hydroxyl ions generated by the bipolar membrane in the S/B loop combine with the remaining bisulfite ions to form the sulfite rich solution for reuse in the absorber 368. The reactions are as follows:

| Salt/base loop: | $Na^+ - HSO_3^- + OH^- = Na_2SO_3$ |
| --- | --- |
| Acid loop: | $HSO_3^- + H^+ = H_2SO_3$ (major) |
| | $SO_3^= + 2H^+ = H_2SO_3$ (minor) |
| | $SO_4^= + 2H^+ = H_2SO_4$ (equivalent to oxidation) |
| | $H_2SO_3 = H_2O + SO_2$ |

The product from the S/B loop comprises the regenerated solution that is forwarded to the absorber. If necessary, the solution can be treated in a cation exchange column to remove the multivalent cations and prevent their build up in the scrubbing solution. The product from the acid loop is stripped to recover $SO_2$ as before.

The process, based on the two compartment anion cell is a one step operation that has important advantages. By using a monovalent selective anion membrane and a large size multivalent chelating agent, such as citric acid, there may be a very low transport/loss of the chelating agent to the acid loop. Secondly, the impurities, such as chlorides, and $No_x$ type anions that are absorbed from the flue gas as well as the sulfate from oxidation, are transported to the acid loop (A) and thus readily purged in a single step, after recovering the $SO_2$.

Purification of Ammonium Salts

In the production of zeolite catalyst supports, a solution of an ammonium salt (e.g. ammonium nitrate or sulfate) is used to convert the zeolite from the sodium to ammonium form. The process requires large quantities of concentrated pure ammonium salt solution and generates a large quantity of a dilute mixed sodium/ammonium salt solution. The resulting mixed salt solution can be processed to recover a pure ammonium salt solution by using a two compartment anion cell, as described in the U.S. Pat. No. 5,228,962. One problem is that the waste mixed salt stream contains multivalent cations (Ca, Mg and rare earth metals) that would precipitate on or beneath the anion surface of the bipolar membrane or within the base loop of the cell, causing longer term operational problems. Furthermore the amounts of these metal ions is fairly high in relation to the concentration of sodium and ammonium ions so that an ion exchange pretreatment to remove these ions can be expensive.

FIG. 11 shows an improved process for purifying the ammonium salts. A salt mixture fed stream, which is usually dilute, is suitably pH adjusted at 378 and filtered at 380. If the salt mixture comprises monovalent anions, say $NH_4NO_3/NaNO_3$, one can use a nanofiltration step to remove any significant amount of the multivalent cations from the solution. If the mixture comprises divalent anions, e.g. $(NH_4)_2SO_4/Na_2SO_4$ an ultrafilter would be the preferred option.

The filtered feed stream is then metered into a recycle tank 381 that feeds the salt/base (S/B) loop of the ED cell 382. A suitable chelating agent such as EDTA is added to the recycle tank. A solution comprising water and recovered ammonia is supplied to the acid loop (A) of the cell. Under a direct current driving force, the anions in the feed stream are transported across the anion membranes 386 in the cell to the acid compartment, where they combine with the protons generated by the bipolar membrane and any ammonia in the feed stream to yield an acidic ammonium salt. Concurrently, the feed stream solution is basified, yielding an ammoniacal solution in a sodium salt background. This solution is forwarded to an ammonia stripper 388. There a stream of air (and optionally the application of heat) is used to strip the ammonia from the sodium salt solution. The recovered ammonia is forwarded to the ammonia absorber 390, while the salt solution from the stripper containing the added chelating agent and the multivalent cations is sent to waste or further processing.

In the absorber, a stream of acidified ammonium salt solution from the ED cell is circulated, in order to absorb the ammonia and obtain the purified ammonium salt solution as shown.

Three pumps P10, P11, P12 are shown in FIG. 11.

Those who are skilled in the art will readily perceive various modifications which fall within the spirit and scope of the invention. Therefore, the appended claims are to be construed to cover all equivalent processes.

What is claimed is:

1. A process for converting a salt solution by eliminating multivalent cation impurities contained therein, said process comprising the steps of: providing a salt solution feed stream, carrying out said process by directing said feed stream into a system including at least a two compartment electrodialysis cell having at least a bipolar membrane and at least a salt loop; and by adding a chelating agent to the salt solution.

2. The process of claim 1 and the further step of adding said chelating agent directly into the loop containing the salt solution.

3. The process of claim 1 wherein the cell further includes an anion exchange membrane and a cation exchange membrane, the salt solution including the added chelating agent is processed within said cell and between said anion exchange membrane and said cation exchange membrane.

4. The process of claim 1 wherein the salt solution is selected from a group consisting of sodium chloride, sodium sulfate potassium chloride, potassium sulfate, sodium nitrate, and potassium nitrate.

5. The process of claim 4 wherein the pH of the selected salt solution is maintained in a range of 2–14.

6. The process of claim 1 wherein the cell includes an ion exchange membrane adjacent said bipolar membrane, and the salt solution including the added chelating agent is contained between an anion selective side of the bipolar membrane and said adjacent ion exchange membrane.

7. The process of claim 1 further comprising the added steps of treating the salt solution to remove insoluble matter and multivalent cation impurities contained therein by making a pH adjustment and filtration, said filtration being selected from a group consisting of nanofiltration, ultrafiltration, and combinations thereof.

8. The process of claim 1 wherein the added chelating agent is a polyaminoacetic acid.

9. A process of claim 8 for purifying ammonium salts comprising the steps of:

a. adding a chelating agent to a contaminated ammonium starting salt solution and feeding the resulting fluid to a salt/base loop of said two compartment electrodialysis cell containing said bipolar membrane and an anion membrane;

b. feeding a liquid comprising water to fluid in an acid loop of the cell;

c. basifying the feed liquid of step a. to obtain an ammonia rich solution and simultaneously to applying a direct current driving force for transporting anions to the acid loop for forming an acidic product solution in the acid loop;

d. stripping the basified solution of step c. to obtain ammonia; and e. absorbing the ammonia from step d. in the acidic solution from (c) so as to obtain a purified ammonium salt solution.

10. The process of claim 9 wherein the starting salt solution of step a. is selected from a group consisting of a mixture of ammonium sulfate and sodium sulfate, and a mixture of ammonium nitrate and sodium nitrate.

11. The process of claim 9 where the salt of the starting solution of step a is a monovalent anion and the anion membrane used in step a. is a monovalent selective membrane.

12. The process of claim 11 comprising the further step of nanofiltering a feed salt stream prior to feeding it into the electrodialysis cell.

13. The process of claim 9 where the chelating agent of step a. is a polyaminoacetic acid.

\* \* \* \* \*

UNITED STATES PATENT AND TRADEMARK OFFICE
CERTIFICATE OF CORRECTION

PATENT NO. : 6,755,951 B1
DATED : June 29, 2004
INVENTOR(S) : K. N. Mani

It is certified that error appears in the above-identified patent and that said Letters Patent is hereby corrected as shown below:

Column 2,
Line 10, after "components" insert -- . --.
Line 17, insert a space between "hydroxyl" and "(OH$^-$)"
Line 27, delete "oxygen( at" and substitute therefor -- oxygen (at --.
Line 29, after "Products" insert -- , --.
Line 31, delete "H+ions" and substitute therefor -- H$^+$ ions --.

Column 3,
Line 7, delete "H$^-$" and substitute therefor -- H$^+$ --.
Line 10, delete "OH" and substitute therefor -- OH$^-$ --.

Column 4,
Line 34, insert a space between "cathode" and "(-)".
Line 35, delete "outline" and substitute therefor -- outlined --.

Column 6,
Line 10, insert a space between "Stone" and "&".
Line 11, delete "PB-242 573," and substitute therefor -- PB-242573, --.

Column 11,
Line 52, after "well" insert -- as --.

Column 12,
Line 22, delete "-the" and substitute therefor -- the --.
Line 34, delete "k$_1$" and substitute therefor -- k$_i$ --.
Line 35, delete "ML$^{n+}$K$_1$=[ML$^{n+]/[Mn+}$]" and substitute therefor -- ML$^{n+}$ K$_1$=[ML$^{n+}$]/[M$^{n+}$] --.
Line 51, delete "-log[M$^{n+]=logK}$$_1$" and substitute therefor -- log[M$^{n+}$]=logK$_1$ --.

Column 13,
Line 7, after "number" insert -- of --.
Line 27, after "operation" insert -- . --.
Line 28, delete "suitable a" and substitute therefor -- a suitable --.

Column 14,
Line 39, after "precipitates" insert -- . --.

UNITED STATES PATENT AND TRADEMARK OFFICE
CERTIFICATE OF CORRECTION

PATENT NO.   : 6,755,951 B1
DATED        : June 29, 2004
INVENTOR(S)  : K. N. Mani It is certified that error appears in the above-identified patent and that said Letters Patent is hereby corrected as shown below:

Column 17,
Table 1, Column 5, delete "-28" and substitute therefor -- ~28 --.
Table 1, Column 5, delete "-26" and substitute therefor -- ~26 --.
Line 24, delete period after "input)".
Line 27, delete "sreams" and substitute therefor -- streams --.
Lines 52-53, delete "Company); or, or AQ" and substitute therefor -- Company); or AQ --.

Column 19,
Line 26, delete "ppm." and substitute therefor -- ppm --.

Column 20,
Line 10, after "Osmonics" insert -- , --.

Column 21,
Line 8, delete "steam" and substitute therefor -- stream --.
Line 25, after "solution" insert -- . --.
Table 4, Column 6, delete each occurrence of "-100" and substitute therefor -- ~100 --.

Column 23,
Line 54, after "portion" insert -- of --.

Column 24,
Line 5, delete "a", first occurrence and substitute therefor -- an --.
Line 19, delete "not", second occurrence.
Lines 19-20, delete "transport" and substitute therefor -- transported --.
Line 29, delete "(28A/ft$^2$" and substitute therefor -- (=28A/ft$^2$ --.

Column 25,
Line 17, delete "Na$_2$S$_4$" and substitute therefor -- Na$_2$SO$_4$ --.
Line 48, delete "Na$^-$" and substitute therefor -- Na$^+$ --.
Line 58, after "returned" insert -- to --.
Line 58, after "order" insert -- to --.

Column 26,
Line 10, after "5-10%" insert -- range --.
Line 12, delete "SO$_3$'" and substitute therefor -- SO$_3^{2-}$ --.
Line 21, delete "construction" and substitute therefor -- constructed --.

UNITED STATES PATENT AND TRADEMARK OFFICE
CERTIFICATE OF CORRECTION

PATENT NO.   : 6,755,951 B1
DATED        : June 29, 2004
INVENTOR(S)  : K. N. Mani It is certified that error appears in the above-identified patent and that said Letters Patent is hereby corrected as shown below:

Column 28,
Line 52, after "step a" insert -- . --.

Signed and Sealed this

Eleventh Day of January, 2005

JON W. DUDAS
*Director of the United States Patent and Trademark Office*